(12) United States Patent
Racchini et al.

(10) Patent No.: US 10,555,811 B2
(45) Date of Patent: Feb. 11, 2020

(54) DELIVERY DEVICE FOR A STENTED PROSTHETIC HEART VALVE

(71) Applicant: Medtronic, Inc., Minneapolis, MN (US)

(72) Inventors: Joel Racchini, Edina, MN (US); Jeffrey Sandstrom, Scandia, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 71 days.

(21) Appl. No.: 15/405,070

(22) Filed: Jan. 12, 2017

(65) Prior Publication Data

US 2017/0196690 A1     Jul. 13, 2017

Related U.S. Application Data

(60) Provisional application No. 62/278,324, filed on Jan. 13, 2016.

(51) Int. Cl.
*A61F 2/24* (2006.01)
*A61M 25/01* (2006.01)

(52) U.S. Cl.
CPC .......... *A61F 2/2436* (2013.01); *A61F 2/2418* (2013.01); *A61M 25/0136* (2013.01); *A61M 25/0144* (2013.01); *A61M 2205/0266* (2013.01)

(58) Field of Classification Search
CPC ...... A61F 2250/0018; A61F 2250/0039; A61F 2/2418; A61F 2/2436; A61F 2/966; A61F 2002/9665; A61F 2/01; A61M 2025/0024; A61M 2205/0266
USPC ....................................................... 623/2.11
See application file for complete search history.

(56) References Cited

U.S. PATENT DOCUMENTS

| | | | |
|---|---|---|---|
| 7,662,186 B2 | 2/2010 | Bagga et al. | |
| 7,740,655 B2 | 6/2010 | Birdsall | |
| 8,579,963 B2 | 11/2013 | Tabor | |
| 8,986,372 B2 * | 3/2015 | Murry, III | ............. A61F 2/2436 623/2.11 |
| 9,192,751 B2 | 11/2015 | Macaulay et al. | |
| 2011/0098804 A1 | 4/2011 | Yeung et al. | |

(Continued)

OTHER PUBLICATIONS

PCT/US2017/013245, "The International Search Report and the Written Opinion of the International Searching Authority" dated Mar. 29, 2017, 14pgs.

*Primary Examiner* — Eric J Rosen
*Assistant Examiner* — Andrew P. Restaino
(74) *Attorney, Agent, or Firm* — Medler Ferro Woodhouse & Mills PLLC

(57) ABSTRACT

A delivery device for percutaneously delivering a stented prosthetic heart valve includes a capsule assembly, a handle, and an outer stability shaft. The capsule assembly includes a capsule and a proximal shaft coupled to the capsule. The capsule includes an expanded configuration wherein the capsule has a first outer diameter, and a collapsed configuration wherein the capsule has a second outer diameter smaller than the first outer diameter. The outer stability shaft defines a lumen and is coupled to the handle and configured to receive the proximal shaft within the lumen of the outer stability shaft. The outer stability shaft has an inner diameter, wherein the first outer diameter of the capsule is greater than the inner diameter of the outer stability shaft and the second outer diameter of the capsule is smaller than the inner diameter of the outer stability shaft.

16 Claims, 33 Drawing Sheets

(56) References Cited

U.S. PATENT DOCUMENTS

| | | | |
|---|---|---|---|
| 2011/0245917 A1* | 10/2011 | Savage | A61F 2/2427 |
| | | | 623/2.11 |
| 2011/0251679 A1 | 10/2011 | Wiemeyer et al. | |
| 2011/0251680 A1* | 10/2011 | Tran | A61F 2/2436 |
| | | | 623/2.11 |
| 2011/0251683 A1 | 10/2011 | Tabor | |
| 2011/0257733 A1 | 10/2011 | Dwork | |
| 2014/0067050 A1 | 3/2014 | Costello et al. | |
| 2014/0128963 A1* | 5/2014 | Quill | A61F 2/2436 |
| | | | 623/2.11 |
| 2014/0236122 A1 | 8/2014 | Anderson et al. | |
| 2014/0236123 A1* | 8/2014 | Birmingham | A61M 25/005 |
| | | | 29/428 |
| 2014/0330368 A1 | 11/2014 | Gloss | |
| 2015/0018939 A1* | 1/2015 | Colson | A61F 2/243 |
| | | | 623/2.11 |
| 2015/0272731 A1* | 10/2015 | Racchini | A61F 2/2418 |
| | | | 623/2.11 |
| 2016/0262885 A1* | 9/2016 | Sandstrom | A61F 2/2436 |

\* cited by examiner

Expanded Configuration

Collapsed Configuration

DELIVERY DEVICE FOR A STENTED PROSTHETIC HEART VALVE

CROSS-REFERENCE TO RELATED APPLICATIONS

This application claims the benefit under 35 U.S.C. § 119(e) of the filing date of U.S. Provisional Application No. 62/278,324 filed Jan. 13, 2016, the contents of which are incorporated by reference herein in their entirety.

FIELD OF INVENTION

The present invention relates to systems and methods for percutaneous transcatheter delivery and implantation of a stented prosthetic heart valve. More particularly, it relates to the delivery device and methods for the centering of a stented prosthetic heart valve within an annulus of a native heart valve.

BACKGROUND

Heart valves are sometimes damaged by disease or by aging, resulting in problems with the proper functioning of the valve. Heart valve replacement has become a routine surgical procedure for patients suffering from valve dysfunctions. Traditional open surgery inflicts significant patient trauma and discomfort, requires extensive recuperation times, and may result in life-threatening complications.

To address these concerns, efforts have been made to perform cardiac valve replacements using minimally-invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter (or transluminal) delivery and implantation of replacement cardiac valves to solve the problems presented by traditional open surgery and minimally-invasive surgical methods. In such methods, a stented prosthetic heart valve is compacted for delivery in a catheter and then advanced, for example through an opening in the femoral artery, and through the descending aorta to the heart, where the stented prosthetic heart valve is then deployed in the valve annulus (e.g., the aortic valve annulus).

Various types and configurations of stented prosthetic heart valves are available for percutaneous valve replacement procedures. In general, stented prosthetic heart valve designs attempt to replicate the function of the valve being replaced and thus will include valve leaflet-like structures. Valve prostheses are generally formed by attaching a bioprosthetic valve to a frame made of a wire or a network of wires. Such a stented prosthetic heart valve can be compressed radially to introduce the stented prosthetic heart valve into the body of the patient percutaneously through a catheter. The stented prosthetic heart valve may be deployed by radially expanding it once positioned at the desired treatment site. If the deployed prosthesis is incorrectly positioned relative to the valve annulus, serious complications may arise, including paravalvular leakage (PVL) or the requirement for placement of a permanent pacemaker.

A standard delivery device for percutaneous transcatheter delivery of a stented prosthetic heart valve is shown in FIGS. 1A-1C. FIG. 1A shows a delivery device 1100 in a delivery configuration. FIG. 1B shows delivery device 1100 with a capsule 1108 retracted. FIG. 1C shows planer or longitudinal movement of capsule 1108 of delivery device 1100. Delivery device 1100 includes a handle 1140, an outer stability shaft 1110, a proximal shaft 1118 coupled to capsule 1108, and an inner shaft 1114. A stented prosthetic heart valve (not shown) in a radially compressed delivery configuration is compressively retained within capsule 1108 for delivery to the treatment site. A gap distance G1 is the distance between a distal end 1126 of outer stability shaft 1110 and a proximal end 1109 of capsule 1108. Gap distance G1 is required to permit retraction of capsule 1108, along a longitudinal axis $LA_d$, to fully release the stented prosthetic heart valve (not shown) as shown in FIG. 1B. Gap distance G1 plus the length of capsule 1108 combine to form a lever arm L1, as shown in FIG. 1A. Stated another way, lever arm L1 includes gap distance G1 and the length of capsule 1108 and extends from distal end 1126 of outer stability shaft 1110 to the distal tip of delivery device 1100.

Prior to release of the stented prosthetic heart valve (not shown) at the treatment site, it may be desired to adjust the centered position of capsule 1108 in relation to a valve annulus utilizing a steering mechanism 1152 of delivery device 1100. Steering mechanism 1152 is actuated with a steering actuator 1148 of handle 1140, as shown in FIG. 1C. However, lever arm L1 may result in an inaccurate or unpredictable steering of capsule 1108 and stented prosthetic heart valve retained therein. More particularly, small movements of steering actuator 1148, combined with the relatively long length of lever arm L1, translate to a relatively large planar movement $PM_{f1}$ or $PM_{r1}$ and a large deflection distance $D_{d1}$ from longitudinal axis $LA_d$, of capsule 1108 and stented prosthetic heart valve retained therein.

Accordingly, there is a need for an improved delivery device design and methods to provide smaller centering adjustment movement of capsule 1108 for more accurate positioning of a stented prosthetic heart valve to reduce the instances of post procedure complications.

SUMMARY OF THE INVENTION

Embodiments hereof relate to a delivery device for percutaneously delivering a stented prosthetic heart valve to the site of a damaged or diseased native valve. The stented prosthetic heart valve is radially expandable from a radially compressed delivery configuration to a radially expanded deployed configuration. The delivery device includes a capsule assembly, a handle, and an outer stability shaft. The capsule assembly includes a capsule and a proximal shaft coupled to a proximal end of the capsule. The capsule includes an expanded configuration wherein the capsule has a first outer diameter and is configured to compressively constrain the stented prosthetic heart valve, and a collapsed configuration wherein the capsule has a second outer diameter smaller than the first outer diameter. The handle includes a housing and an actuator mechanism, wherein the actuator mechanism is coupled to a proximal portion of the proximal shaft and is configured to selectively move the proximal shaft and the capsule relative to the housing to release the stented prosthetic heart valve. The outer stability shaft defines a lumen and is coupled to the handle and configured to receive the proximal shaft within the lumen of the outer stability shaft, the outer stability shaft having an inner diameter, wherein the first outer diameter of the capsule is greater than the inner diameter of the outer stability shaft and the second outer diameter of the capsule is smaller than the inner diameter of the outer stability shaft.

Embodiments hereof also relate to a delivery device for percutaneously delivering a stented prosthetic heart valve to the site of a damaged or diseased native valve. The stented prosthetic heart valve is radially expandable from a radially compressed delivery configuration to a radially expanded deployed configuration. The delivery device includes a capsule assembly, a handle, and an outer stability shaft. The capsule assembly includes a capsule and a proximal shaft coupled to a proximal end of the capsule. The capsule includes an expanded configuration wherein the capsule is configured to compressively constrain the stented prosthetic heart valve in the radially compressed delivery configuration, and a collapsed configuration wherein the capsule does not surround the stented prosthetic heart valve. The handle includes a housing and an actuator mechanism, wherein the actuator mechanism is coupled to a proximal portion of the proximal shaft and is configured to selectively move the proximal shaft and the capsule relative to the housing to release the stented prosthetic heart valve. The outer stability shaft defines a lumen and is coupled to the handle and configured to receive the proximal shaft within the lumen of the outer stability shaft. The proximal end of the capsule is disposed distal to a distal end of the outer stability shaft when the capsule is in the expanded configuration and the capsule is disposed within the lumen of the outer stability shaft when the capsule is in the collapsed configuration.

Embodiments hereof also relate to a method for manipulating a delivery device loaded with a radially expandable stented prosthetic heart valve in a radially compressed delivery configuration, through a patient's vasculature, to a treatment site. The stented prosthetic heart valve includes a stent frame to which a valve structure is attached. The delivery device, in the delivery configuration, includes a capsule constraining the stented prosthetic heart valve and having a first outer diameter, and a proximal shaft extending proximally from a proximal end of the capsule. The delivery device further includes an outer stability shaft surrounding the proximal shaft in the delivery configuration, with a distal end of the outer stability shaft terminating proximal of the capsule. The capsule is retracted proximally to release the stented prosthetic heart valve from the capsule. The capsule slides relative to the outer stability shaft to a collapsed configuration with a second outer diameter smaller than the first outer diameter. The capsule is retracted within the outer stability shaft.

DETAILED DESCRIPTION

Specific embodiments of the present invention are now described with reference to the figures, wherein like reference numbers indicate identical or functionally similar elements. The terms "distal" and "proximal", when used in the following description to refer to a catheter or delivery device, are with respect to a position or direction relative to the treating clinician. Thus, "distal" and "distally" refer to positions distant from, or in a direction away from, the clinician and "proximal" and "proximally" refer to positions near, or in a direction toward, the clinician.

The following detailed description is merely exemplary in nature and is not intended to limit the invention or the application and uses of the invention. Furthermore, there is no intention to be bound by any expressed or implied theory presented in the preceding technical field, background, brief summary, or the following detailed description.

As referred to herein, the stented prosthetic heart valves used in accordance with and/or as part of the various systems, devices, and methods of the present disclosure may include a wide variety of different configurations, such as a bioprosthetic heart valve having tissue leaflets or a synthetic heart valve having polymeric, metallic, or tissue-engineered leaflets, and can be specifically configured for replacing any heart valve.

In general terms, the stented prosthetic heart valve of the present disclosure includes a stent supporting a valve structure which may be constructed from tissue and/or synthetic materials, with the stented prosthetic heart valve having a radially expanded deployed configuration that is collapsible to a radially compressed delivery configuration for loading within a delivery device. The stented prosthetic heart valve is usually constructed from a self-expanding material that is configured to self-deploy or expand when released from the delivery device. For example, the stented prosthetic heart valve useful with the present disclosure can be a stented prosthetic heart valve sold under the trade name CoreValve® available from Medtronic CoreValve, LLC. Other non-limiting examples of the stented prosthetic heart valves useful with the systems, devices, and methods of the present disclosure are described in U.S. Pat. No. 7,662,186 to Bragga and U.S. Pat. No. 7,740,655 to Birdsall, each of which are incorporated in their entirety by reference herein. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured.

Figure 2A:
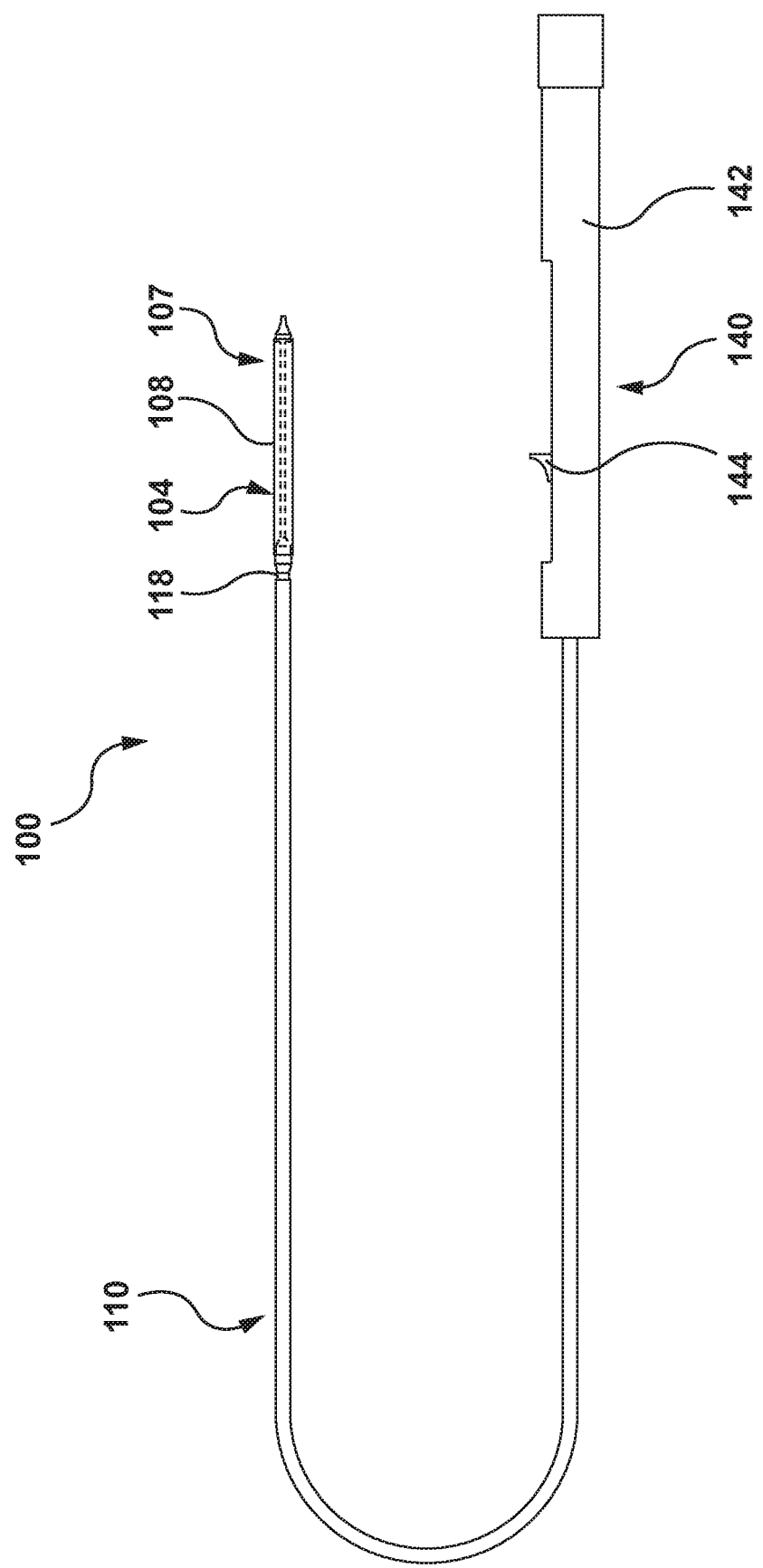
FIG. 2A is a side illustration of an embodiment of a delivery device according to an embodiment hereof, wherein a capsule of the delivery device is in an expanded configuration and disposed distal to a distal end of an outer stability shaft of the delivery device.
Figure 2B:
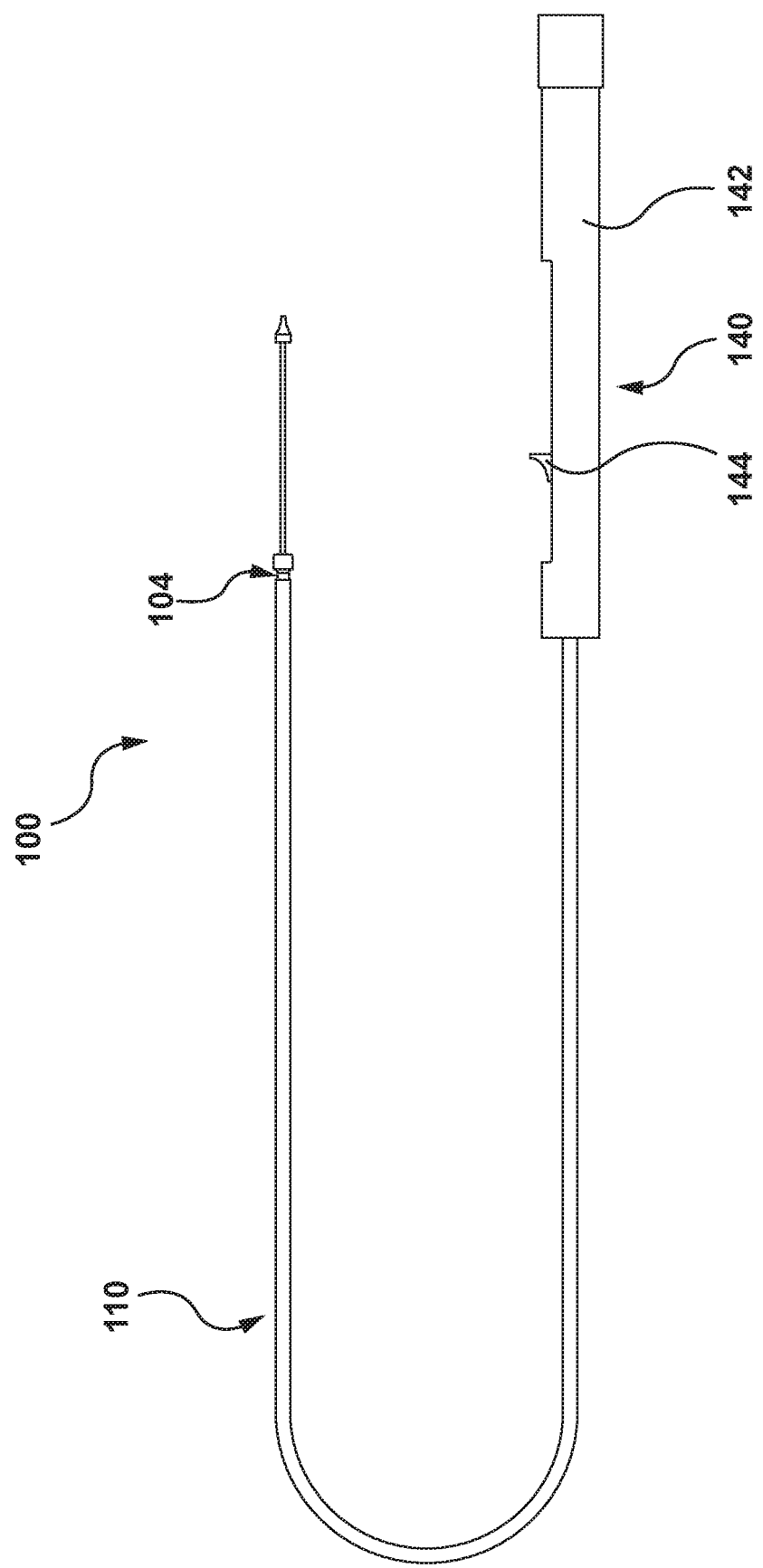
FIG. 2B is a side illustration of the delivery device of FIG. 2A, wherein the capsule is in a collapsed configuration and disposed within the outer stability shaft of the delivery device.

With the above understanding of the stented prosthetic heart valve in mind, a delivery device 100 is shown in FIGS. 2A and 2B. Delivery device 100 includes an outer stability shaft 110 and a capsule 108 for percutaneously delivering and implanting a stented prosthetic heart valve (not shown) according to an embodiment of the present invention. FIG. 2A illustrates delivery device 100 prior to retraction of capsule 108, with capsule 108 being in an expanded configuration, and FIG. 2B illustrates delivery device 100 after retraction of capsule 108 (not shown in FIG. 2B) with capsule 108 being in a collapsed configuration within outer stability shaft 110, as will be described in more detail herein. Capsule 108 is thus configured to transition between the expanded configuration in which capsule 108 is disposed distal to outer stability shaft 110 such that the capsule surrounds and compressively retains a stented prosthetic heart valve, and the collapsed configuration in which the capsule is proximally retracted into outer stability shaft 110. Since capsule 108 is configured to be collapsed on retraction thereof into outer stability shaft 110, capsule 108 may be disposed directly adjacent to the distal end of stability shaft 110 as will be described in more detail herein.

Delivery device 100 includes a handle 140, outer stability shaft 110, a capsule assembly 107, and an inner shaft assembly 104. Components in accordance with the embodiment of delivery device 100 of FIGS. 2A and 2B are presented in greater detail in FIGS. 3-4C. Various features of the components of delivery device 100 reflected in FIGS. 3-4C and described below can be modified or replaced with differing structures and/or mechanisms. Delivery device 100, described in greater detail below, is merely an exemplary embodiment of a transcatheter delivery device according to an embodiment hereof and modifications can be made to the embodiments described herein, without departing from the spirit and scope of the present invention. The present disclosure is in no way limited to capsule assembly 107, inner shaft assembly 104, outer stability shaft 110, and handle 140, shown and described below. Components of delivery device 100 may assume different forms and construction based upon application needs as described in greater detail in U.S. Pat. No. 7,662,186 to Bragga and U.S. Pat. No. 7,740,655 to Birdsall, each of which were previously incorporated by reference. Therefore, the following detailed description is not meant to be limiting. Further, the systems and functions described below can be implemented in many different embodiments of hardware. Any actual hardware described is not meant to be limiting. The operation and behavior of the systems and methods presented are described with the understanding that modifications and variations of the embodiments are possible given the level of detail presented.

Figure 3:
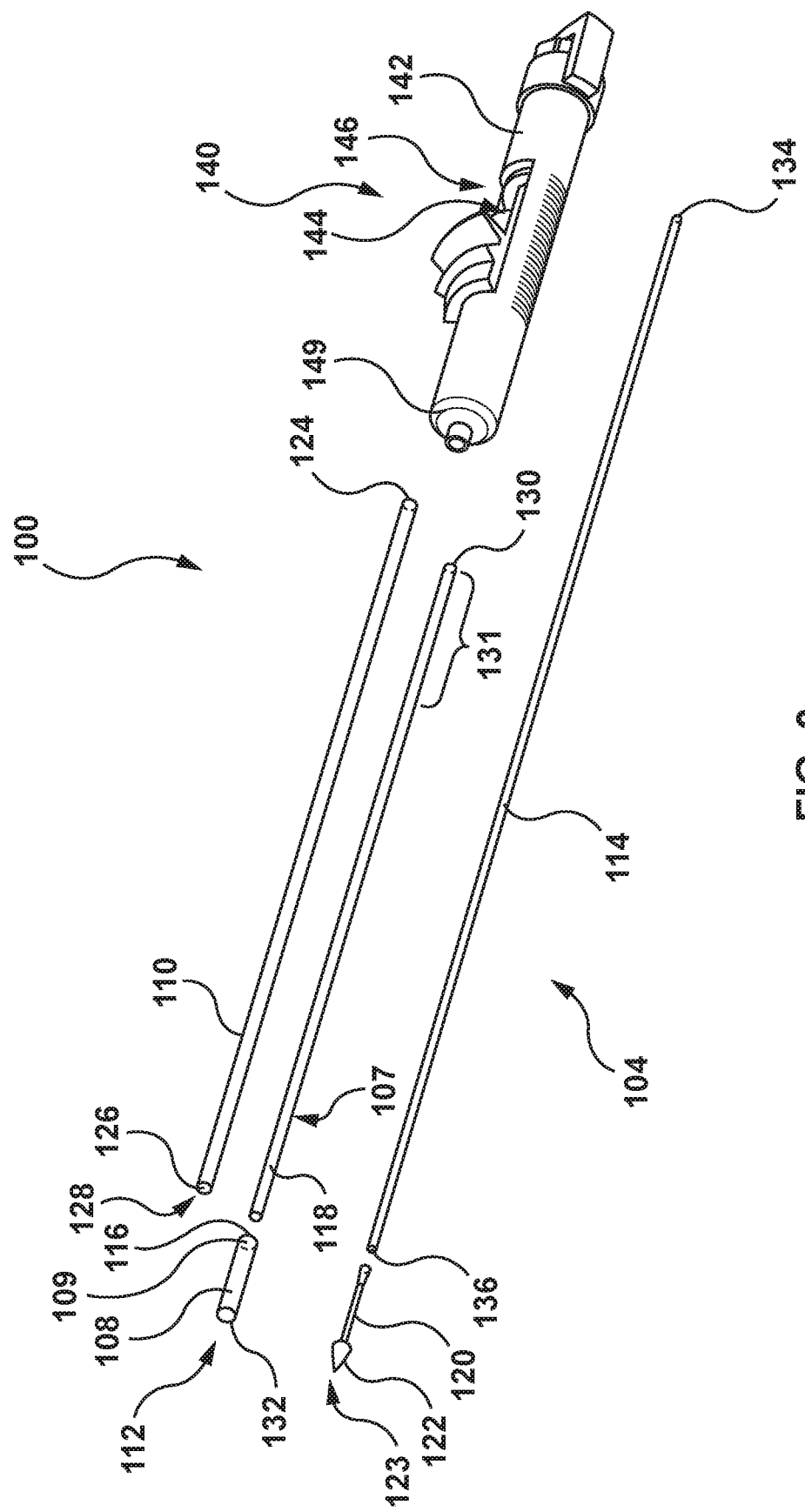
FIG. 3 is an exploded perspective illustration of the delivery device of FIG. 2A.
Figure 4A:
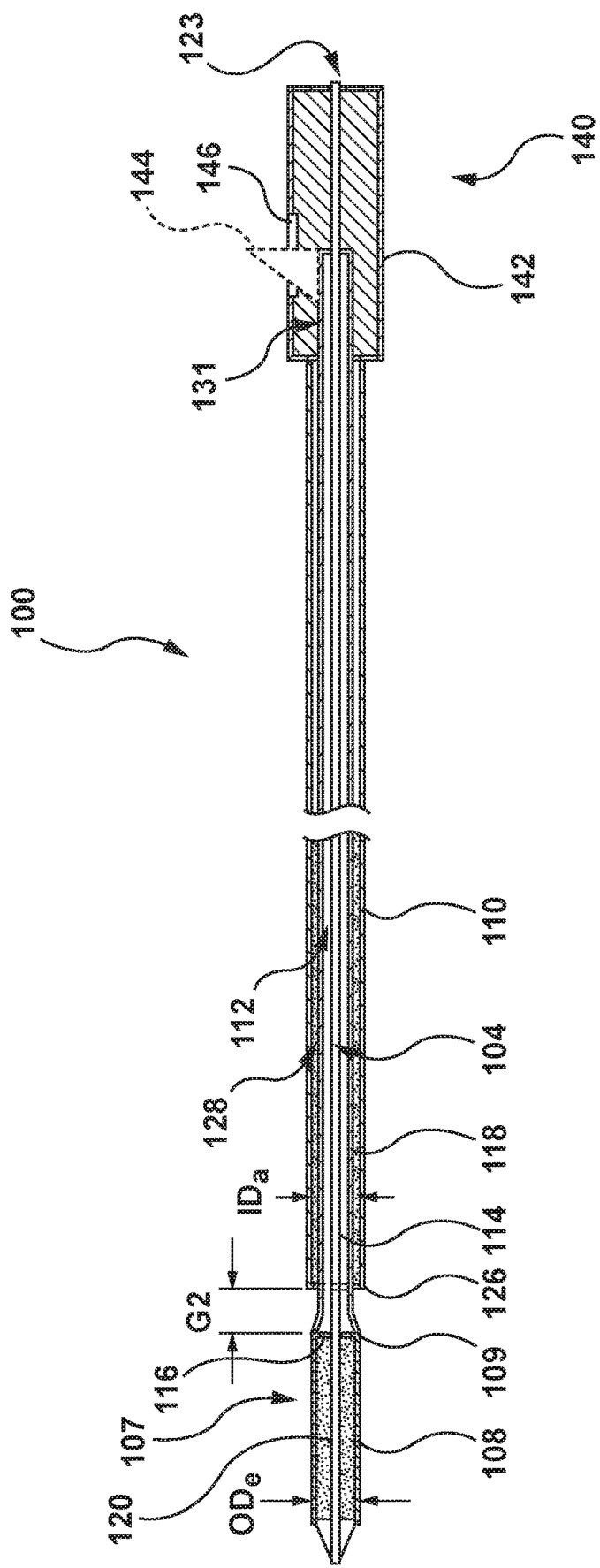
FIG. 4A is a cutaway illustration of the delivery device of FIG. 2A with the capsule in the expanded configuration and disposed distal to the distal end of the outer stability shaft of the delivery device.
Figure 4B:
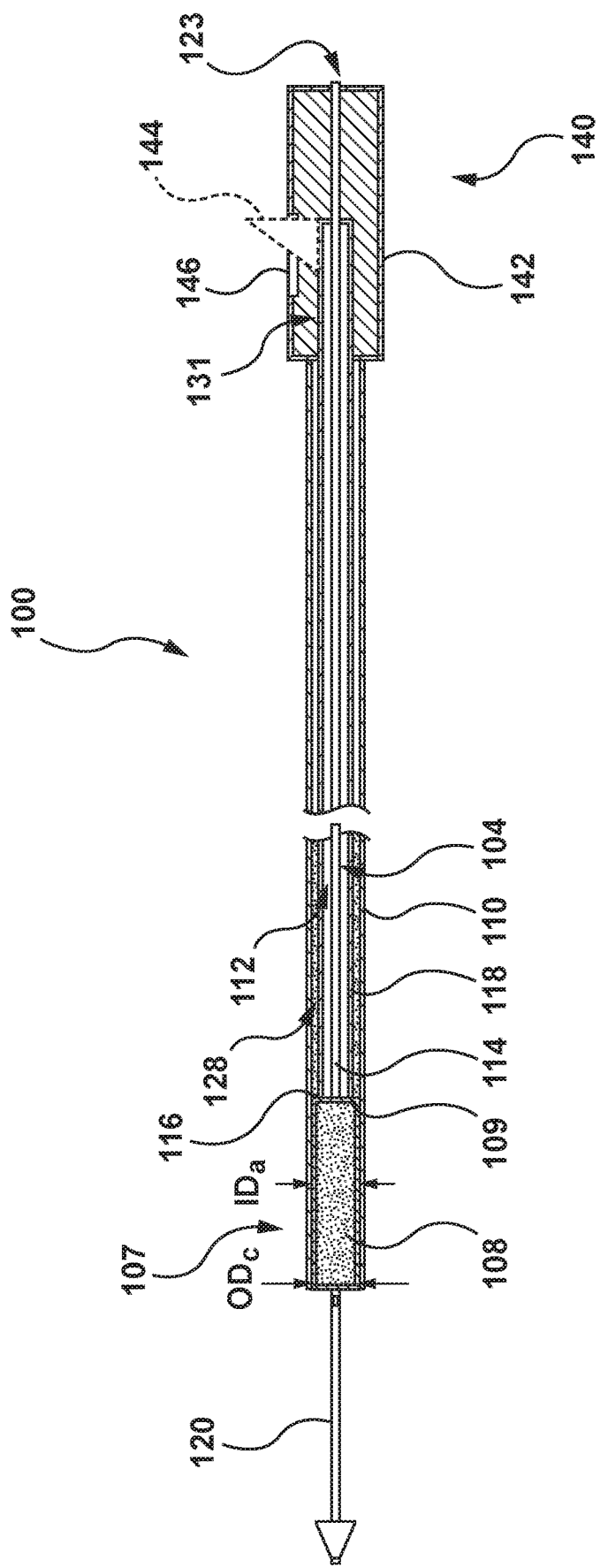
FIG. 4B is a cutaway illustration of the delivery device of FIG. 2B with the capsule in the collapsed configuration and disposed within the outer stability shaft of the delivery device.

Handle 140 includes a housing 142 and an actuator mechanism 144 retained therein. More particularly, handle 140 is configured to maintain portions of actuator mechanism 144 within a cavity (not shown), defined by housing 142, as shown in FIGS. 2A and 2B. In the embodiment shown in FIGS. 3-4B, housing 140 further forms a longitudinal slot 146 through which actuator mechanism 144 extends for interfacing by a user. Handle 140 provides a surface for convenient handling and grasping by a user, and can have a generally cylindrical shape as shown. While handle 140 of FIGS. 3-4B is shown with a cylindrical shape, it is not meant to limit the design, and other shapes and sizes are contemplated based on the application requirements. Handle 140 can assume a variety of configurations described in greater detail in U.S. Pat. No. 8,579,963 to Tabor, which is incorporated in its entirety by reference herein. Actuator mechanism 144 is generally constructed to provide selective retraction/advancement of capsule assembly 107 and can have a variety of constructions and/or devices capable of providing the desired user interface. Actuator mechanism 144 is further described in U.S. Pat. No. 8,579,963 to Tabor, previously incorporated by reference.

Figure 4C:
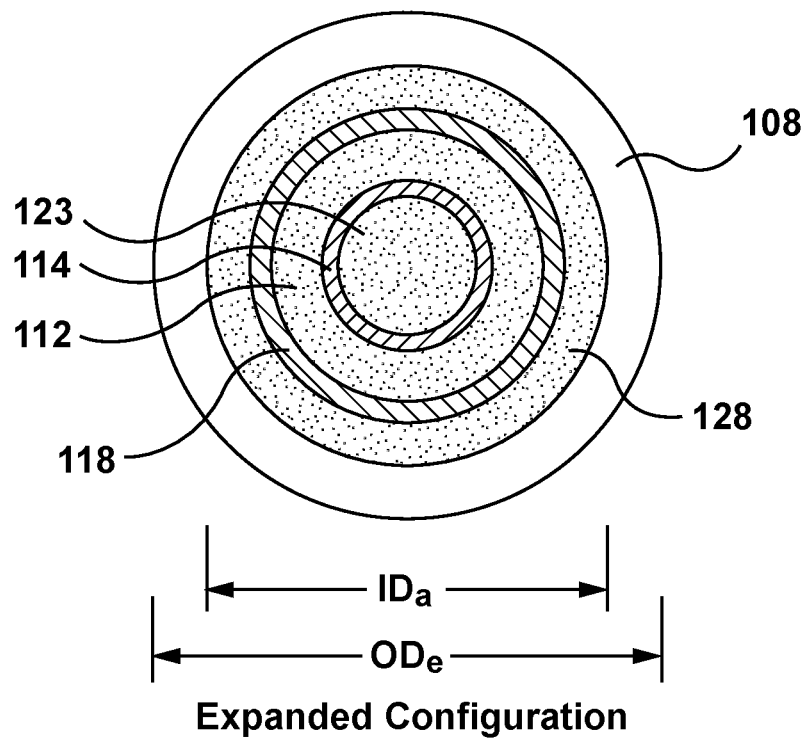
FIG. 4C is an end view of the delivery device of FIG. 2A comparing the capsule's expanded configuration and collapsed configuration.
Figure 4C:
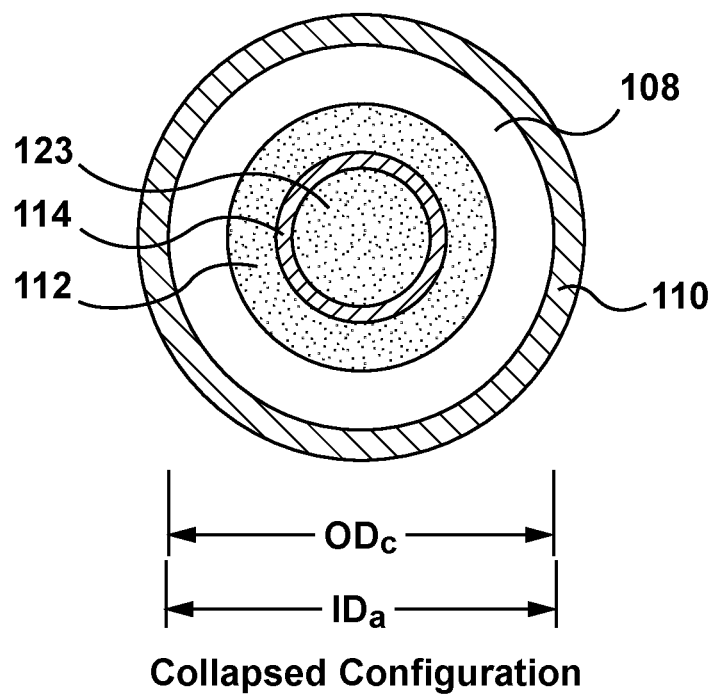

Capsule assembly 107 is coaxially and slidably disposed between inner shaft assembly 104 and outer stability shaft 110. Stated another way, capsule assembly 107 may be longitudinally moved relative to inner shaft assembly 104 and outer stability shaft 110 as described in more detail herein. With reference to FIGS. 3-4C, capsule assembly 107 includes capsule 108 and a proximal shaft 118, and defines a lumen 112 extending from a proximal end 130 of proximal shaft 118 to a distal end 132 of capsule 108. Although capsule assembly 107 is described herein as including capsule 108 and proximal shaft 118, capsule 108 may simply be an extension of proximal shaft 118. The length and thickness of capsule 108 are determined by the requirements of the specific application. Proximal shaft 118 is configured for fixed connection to capsule 108 at a connection point 116 at a proximal end 109 of capsule 108 for example, and not by way of limitation, by fusing, welding, adhesive, sutures, or other means suitable for the purposes described herein, and extends proximally from capsule 108, with proximal shaft 118 configured for fixed connection to handle 140. More particularly, proximal shaft 118 of capsule assembly 107 extends proximally into housing 142 of handle 140 and a proximal portion 131 of proximal shaft 118 is rigidly connected to actuator mechanism 144 of handle 140. Proximal portion 131 is coupled to actuator mechanism 144 such that movement of actuator mechanism 144 causes capsule assembly 107 to move relative to outer stability shaft 110 and inner shaft assembly 104. Proximal shaft 118 may be coupled to actuator mechanism 144, for example, and not by way of limitation by adhesives, welding, clamping, and other coupling devices as appropriate. Capsule assembly 107 is thus movable relative to handle 140, outer stability shaft 110, and inner shaft assembly 104 by actuator mechanism 144. However, if actuator mechanism 144 is not moved and handle 140 is moved, capsule assembly 107 moves with handle 140, not relative to handle 140.

Inner shaft assembly 104 extends within lumen 112 of capsule assembly 107. Inner shaft assembly 104 includes an inner shaft 114, a retention member 120, and a tip 122. Inner shaft 114 extends from a proximal end 134 of inner shaft 114 to a distal end 136 of inner shaft 114. Distal end 136 of inner shaft 114 connects or is attached to retention member 120, and retention member 120 connects or is attached to tip 122. The components of inner shaft assembly 104 combine to define a continuous lumen 123, which is sized to receive an auxiliary component such as a guidewire (not shown). Although inner shaft assembly 104 is described herein as including inner shaft 114, retention member 120, and tip 122, retention member 120 and tip 122 may simply be an extension of inner shaft 114. Inner shaft 114 of inner shaft assembly 104 extends proximally through housing 142 of handle 140, and is rigidly connected to handle 140 such that lumen 123 provides access for auxiliary components (e.g., a guidewire) therein. Inner shaft 114 may be coupled to handle 140, for example, and not by way of limitation, by adhesives, welding, clamping, and other coupling devices as appropriate. During sliding or longitudinal movement of capsule assembly 107 relative thereto, inner shaft assembly 104 is fixed relative to handle 140. Inner shaft assembly 104 can assume a variety of configurations described in greater detail in U.S. Pat. No. 8,579,963 to Tabor, previously incorporated by reference.

Outer stability shaft 110 is disposed over a portion of capsule assembly 107. Outer stability shaft 110 extends distally from handle 140, and encompasses and surrounds a portion of the length of proximal shaft 118, thus stabilizing at least a portion of proximal shaft 118 as shown in FIG. 4A such that outer stability shaft 110 provides stability to delivery device 100. Outer stability shaft 110 has a proximal end 124 and a distal end 126 that defines a lumen 128 therein. Lumen 128 of outer stability shaft 110 is sized to coaxially receive capsule assembly 107, and in particular proximal shaft 118, in a manner permitting the sliding of proximal shaft 118 relative to outer stability shaft 110. Outer stability shaft 110 is configured for fixed connection to handle 140. More particularly, handle 140 has a distal end 149 configured to accept proximal end 124 of outer stability shaft 110. Outer stability shaft 110 may be coupled to handle 140, for example, and not by way of limitations, by adhesives, welding, clamping, and other coupling devices, as appropriate. Outer stability shaft 110 can assume a variety of configurations described in greater detail in U.S. Pat. No. 8,579,963 to Tabor, previously incorporated by reference.

According to embodiments hereof, capsule 108 is configured to be collapsible upon retraction thereof into outer stability shaft 110. FIG. 4A shows delivery device 100 with capsule 108 in the expanded configuration, in which a stented prosthetic heart valve (not shown) in a radially compressed delivery configuration is loaded therein. As shown in FIGS. 4A and 4C, when in the expanded configuration, capsule 108 has an outer diameter ODe and is coaxially disposed over retention member 120 of inner shaft assembly 104. Outer diameter ODe is greater than an inner diameter IDa of outer stability shaft 110. The capsule 108 in the expanded configuration has an inner diameter along an entire length of the capsule 108 that is not greater than an outer diameter ODe of the outer stability shaft 110. However, when capsule 108 is in the collapsed configuration, as shown in FIGS. 4B and 4C, capsule 108 has an outer diameter ODE, which is smaller than inner diameter IDa of outer stability shaft 110. More particularly, as previously described, capsule assembly 107, including capsule 108 and proximal shaft 118, can be retracted in a proximal direction relative to inner shaft assembly 104, outer stability shaft 110, and housing 142 of handle 140 such that capsule 108 is proximally retracted into outer stability shaft 110 as shown in FIG. 4B. When retracted, capsule 108 collapses to outer diameter $OD_c$, which is smaller than inner diameter IDa of outer stability shaft 110. Thus, capsule 108 transitions from the expanded configuration of FIG. 4A to the collapsed configuration of FIG. 4B when retracted into lumen 128 of outer stability shaft 110. Capsule 108 retracts into lumen 128 of outer stability shaft 110 such that capsule 108 does not surround the stented prosthetic heart valve (not shown), and the stented prosthetic heart valve (not shown) radially expands to its radially expanded deployed configuration. Thus, capsule 108 is in its expanded configuration prior to retraction of capsule assembly 107 and release of the stented prosthetic heart valve, and capsule 108 is in its collapsed configuration after retraction of capsule assembly 107 and release of the stented prosthetic heart valve. FIG. 4C shows an end view comparison of capsule 108 in the expanded and collapsed configurations. In the expanded configuration, capsule 108 with outer diameter ODe is shown in relation to lumen 123 of inner shaft 114, lumen 112 of proximal shaft 118, and lumen 128 of outer stability shaft 110 (obscured in FIG. 4C by capsule 108 in the expanded configuration). In the collapsed configuration, capsule 108 with outer diameter ODD is shown in relation to lumen 123 of inner shaft 114, lumen 112 of proximal shaft 118 (obscured by capsule 108 in the collapsed configuration), and outer stability shaft 110.

Since capsule 108 is configured to be collapsible upon retraction thereof into outer stability shaft 110, distal end 126 of outer stability shaft 110 may be disposed directly adjacent to proximal end 109 of capsule 108. Stated another way, since capsule 108 is configured to be collapsible upon retraction thereof into outer stability shaft 110, it is not required to leave a gap between distal end 126 of outer stability shaft 110 and proximal end 109 of capsule 108 sufficient to permit retraction of capsule 108. Rather, outer stability shaft 110 extends such that gap distance G2, as shown in FIG. 4A, between proximal end 109 of capsule 108 and distal end 126 of outer stability shaft 110, is minimized and in the range of 0 mm to 10 mm. Gap distance G2 accommodates a smooth but relatively short taper between capsule 108 and proximal shaft 118 as shown in FIG. 4A. As such, as used herein, "directly adjacent" includes when distal end 126 of outer stability shaft 110 is disposed between 0 mm and 10 mm relative to proximal end 109 of capsule 108. In an embodiment, distal end 126 of outer stability shaft 110 may abut against or contact proximal end 109 of capsule 108.

Figure 7A:
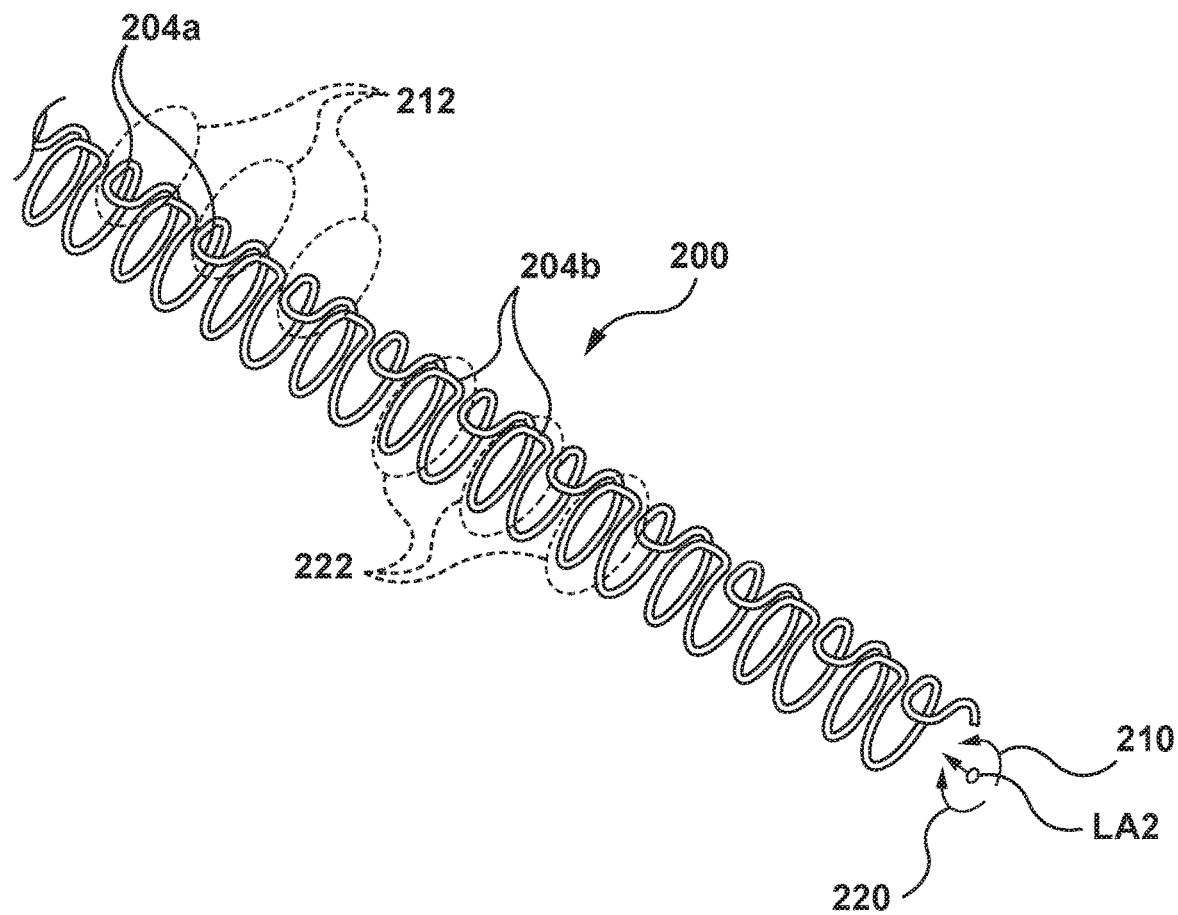
FIG. 7A is a perspective view of the wire structure of FIG. 6A.
Figure 7B:
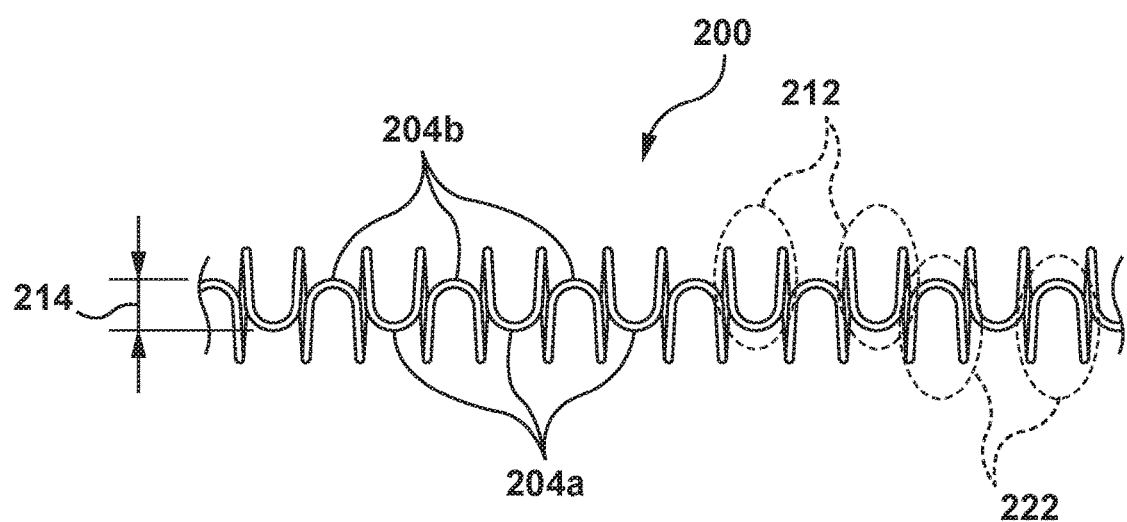
FIG. 7B is a top view of the wire structure of FIG. 6A.
Figure 8A:
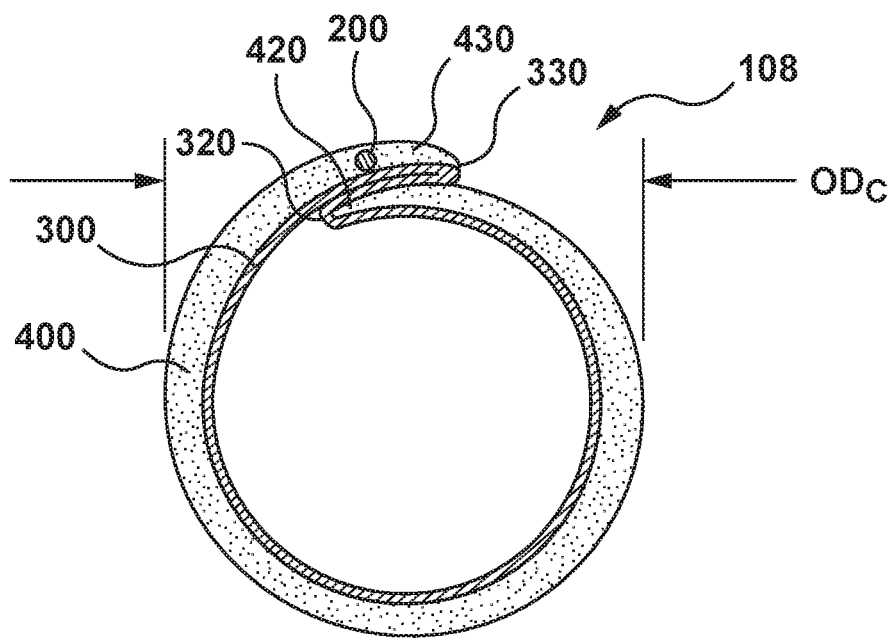
FIG. 8A is an end view of the capsule of FIG. 5, wherein the capsule is shown in the collapsed configuration.
Figure 8B:
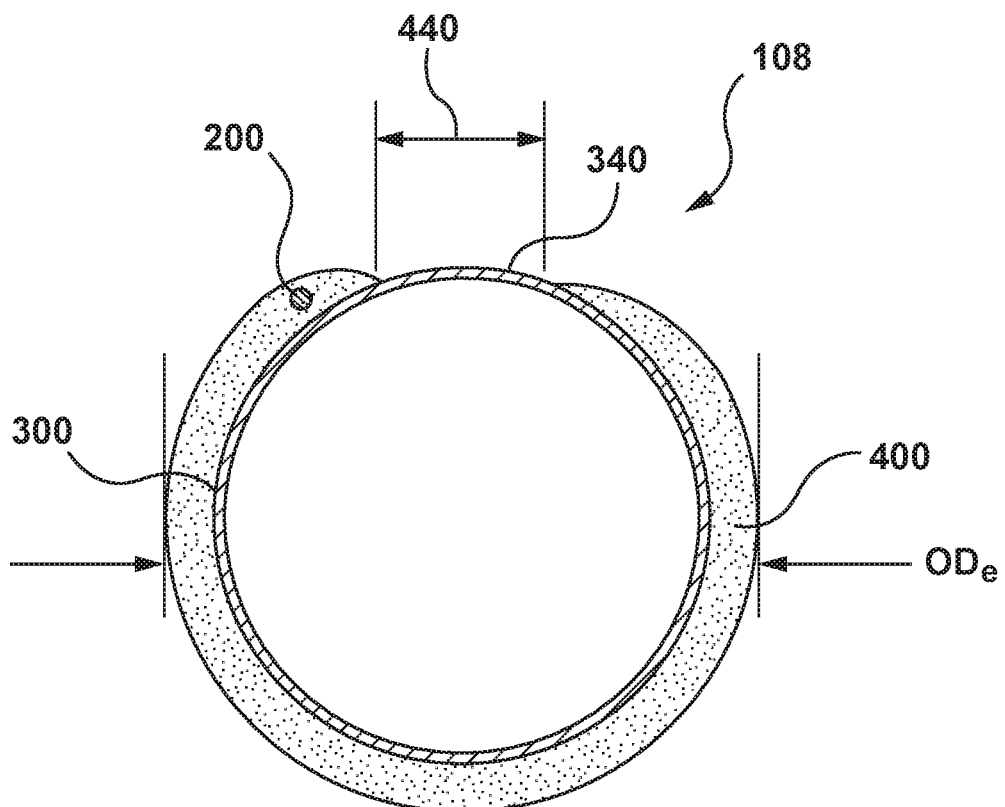
FIG. 8B is an end view of the capsule of FIG. 5, wherein the capsule is shown in the expanded configuration.

FIGS. 5-8B illustrate how capsule 108 is configured to be collapsible upon retraction thereof into outer stability shaft 110 (not shown in FIGS. 5-8B) according to an embodiment hereof. More particularly, capsule 108 includes a wire structure 200, a liner 300, and a jacket 400. Wire structure 200 is coupled between liner 300 and jacket 400, for example, and not by way of limitation, by lamination, embedding, or other methods suitable for the purposes described herein. Liner 300 may be constructed, for example, and not by way of limitation, of Teflon®, polytetrafluoroethylene (PTFE), polyethylene, polyethylene terephthalate (PET), polyester, or other materials suitable for the purposes of the present disclosure. Jacket 400 may be constructed, for example, and not by way of limitation, of polyurethane (e.g. Peliethane©, Elasthane™, Texin®, Tecothane®), polyamide polyether block copolymer (e.g. Pebax®, nylon 12), polyethylene, or other materials suitable for the purposes of the present disclosure. The material for jacket 400 may also include materials to add radiopacity so that capsule 108 can be radio detectable (radiopaque). Wire structure 200 may be formed, for example, and not by way of limitation, of nickel titanium, Nitinol, nickel-cobalt-chromium-molybdenum (MP35N), stainless steel, high spring temper steel, or any other metal or elastomer or composite having elastic properties to permit extension and recoil suitable for purposes of the present disclosure. Wire structure 200 is of a shape memory material with a pre-set shape. In an embodiment, wire structure 200 has a pre-set shape in the collapsed configuration with outer diameter $OD_c$, as shown in FIG. 8A. Wire structure 200 allows capsule 108 to expand to outer diameter $OD_e$ when in the expanded configuration, as shown in FIG. 8B, with the stented prosthetic heart valve (not shown) in the radially compressed delivery configuration within capsule 108. Due to the shape memory material and pre-set shape thereof, wire structure 200 causes capsule 108 to actively recoil to the reduced outer diameter $OD_c$ after release of the stented prosthetic heart valve from capsule 108. As previously stated, outer diameter $OD_e$ is greater than outer diameter $OD_c$ and outer diameter $OD_c$ is smaller than the inner diameter $ID_a$ of outer stability shaft 110.

While wire structure 200 has been previously described with a pre-set shape in the collapsed configuration with outer diameter $OD_c$, this is not meant to limit the design, and wire structure 200 can alternatively have a pre-set shape in the expanded configuration with outer diameter $OD_e$, or any other configuration between the collapsed and expanded configuration based upon the application.

Figure 5:
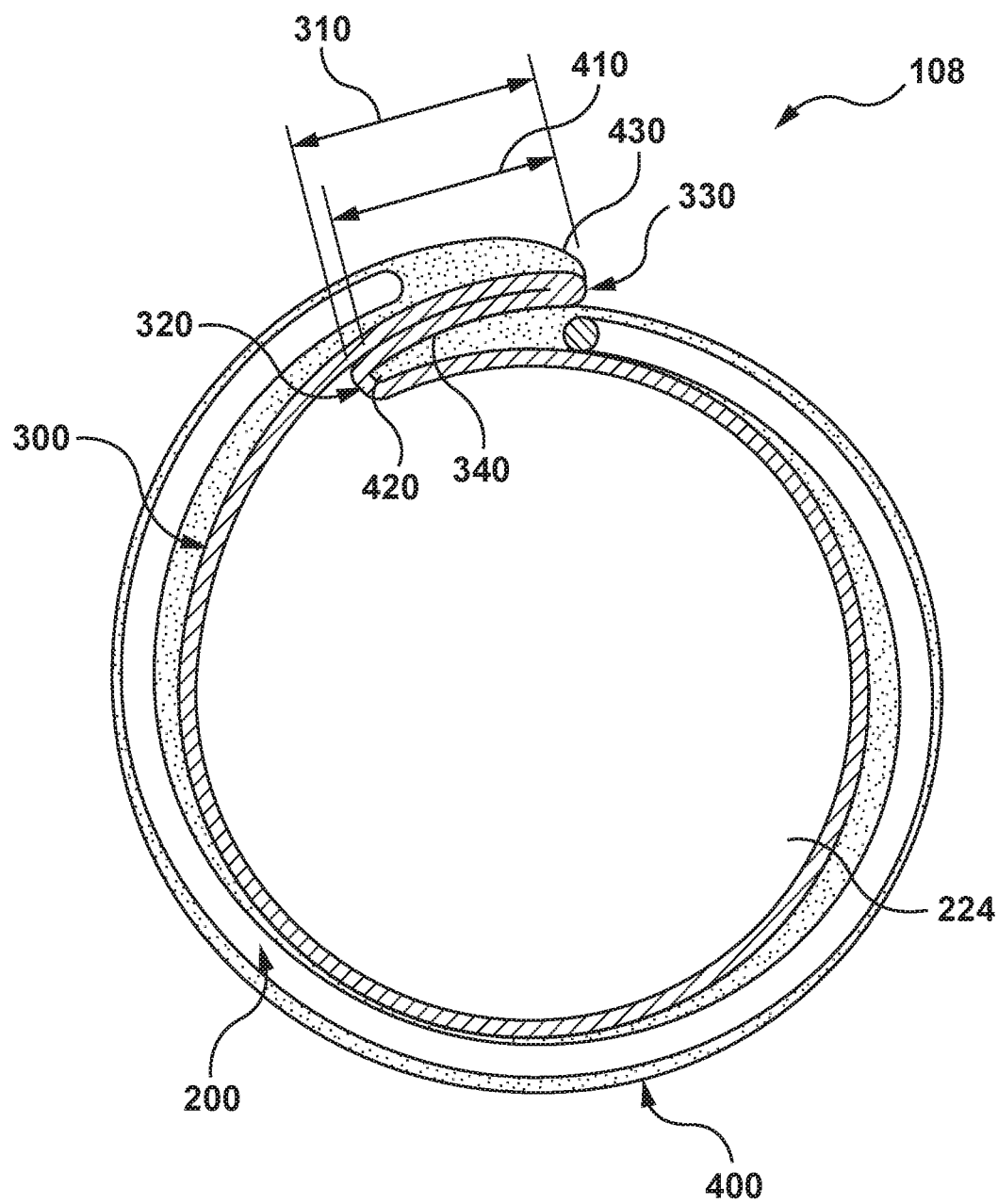
FIG. 5 is an end view of the capsule of the delivery device of FIG. 2A, wherein the capsule is shown in the collapsed configuration.

Liner 300 is circumferentially continuous and forms a lumen 224, as shown in FIG. 5. Wire structure 200 and jacket 400 are non-circumferentially continuous and includes a jacket gap 440 visible in the expanded configuration, as shown in FIG. 8B. In the collapsed configuration, as shown in FIG. 5, capsule 108 includes a liner overlap region 310 and a jacket overlap region 410. Liner overlap region 310 includes a liner gap portion 340 defined by an inner fold 320 and an outer fold 330 of liner 300. Liner gap portion 340 can be at least partially covered by jacket 400. Liner 300 extends around an inner edge 420 to form inner fold 320. Jacket overlap region 410 is defined by inner edge 420 and an outer edge 430 of jacket 400. In the expanded configuration, inner edge 420 and outer edge 430 are separated circumferentially to form jacket gap 440, as shown in FIG. 8B. In such a configuration, inner fold 320 and outer fold 330 are flattened or stretched apart to allow liner gap portion 340 to extend across jacket gap 440.

Figure 6A:
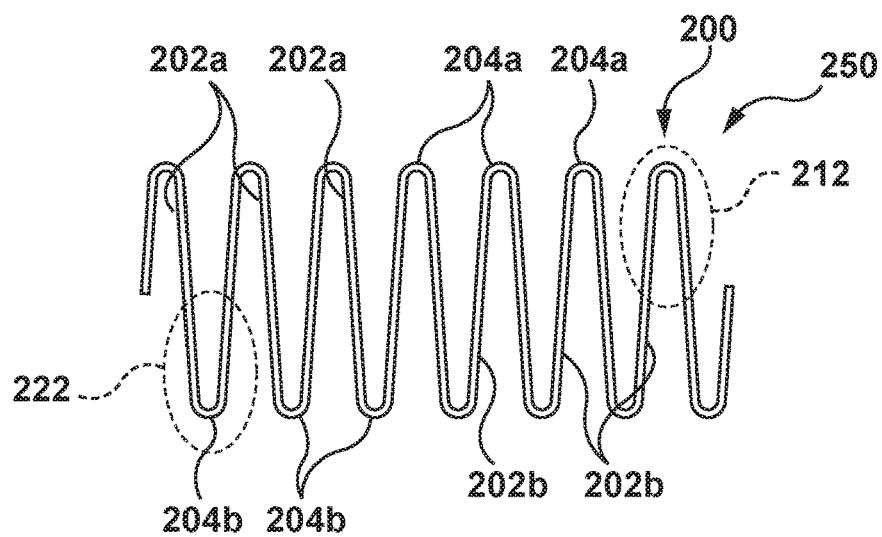
FIG. 6A is a front view of a wire structure of the capsule of FIG. 5, wherein the wire structure is laid out flat for illustrative purposes only.

As previously stated, wire structure 200 has a pre-set shape that allows capsule 108 to collapse to reduced outer diameter $OD_c$ after release of the stented prosthetic heart valve from capsule 108. More particularly, as shown in FIGS. 6-7, wire structure 200 includes a repeating longitudinal pattern and is shown in a flat, or uncurved, state. For example, and not by way of limitation, wire structure 200 may include a sinusoid pattern 250 (FIG. 6A), a square pattern 260 (FIG. 6B), a modified square pattern 270 including a spine 276 (FIG. 6C), a modified square pattern 280 including a preferential bend portion (FIG. 6D), and a modified square pattern 290 including a stepped portion (FIG. 6E). Sinusoid pattern 250, as shown in FIG. 6A, includes a series of alternating adjacent straight portions 202a and 202b. Each straight portion 202a is joined to a first adjacent straight portion 202b by a first bent end portion 204a, and to a second adjacent straight portion 202b by a second bent end portion 204b. Conversely, each straight portion 202b is joined to two straight portions 202a by first bent end portion 204a and second bent end portion 204b.

Figure 6B:
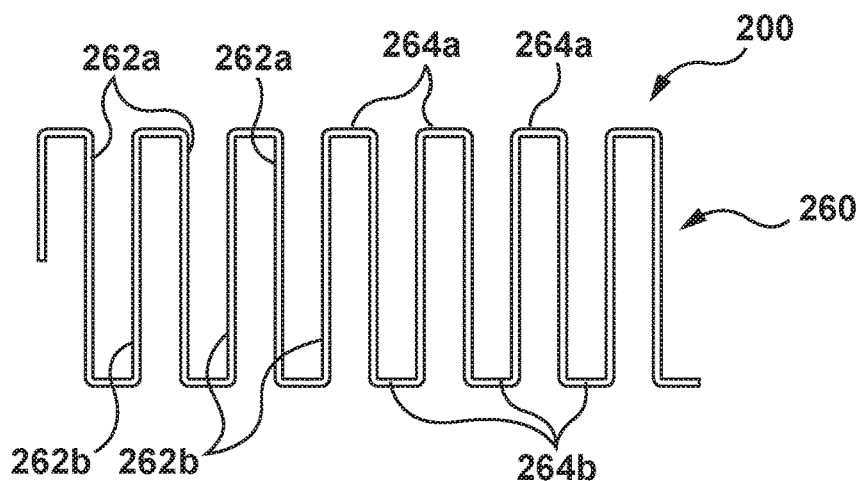
FIG. 6B is a front view of a wire structure of a capsule according to another embodiment hereof, wherein the wire structure is laid out flat for illustrative purposes only.

Square pattern 260, as shown in FIG. 6B, includes a series of alternating adjacent straight portions 262a and 262b. Each straight portion 262a is joined to a first adjacent straight portion 262b by a first end portion 264a, and to a second adjacent straight portion 262b by a second end portion 264b. Conversely, each straight portion 262b is joined to two straight portions 262a by first end portion 264a and second end portion 264b.

Figure 6C:
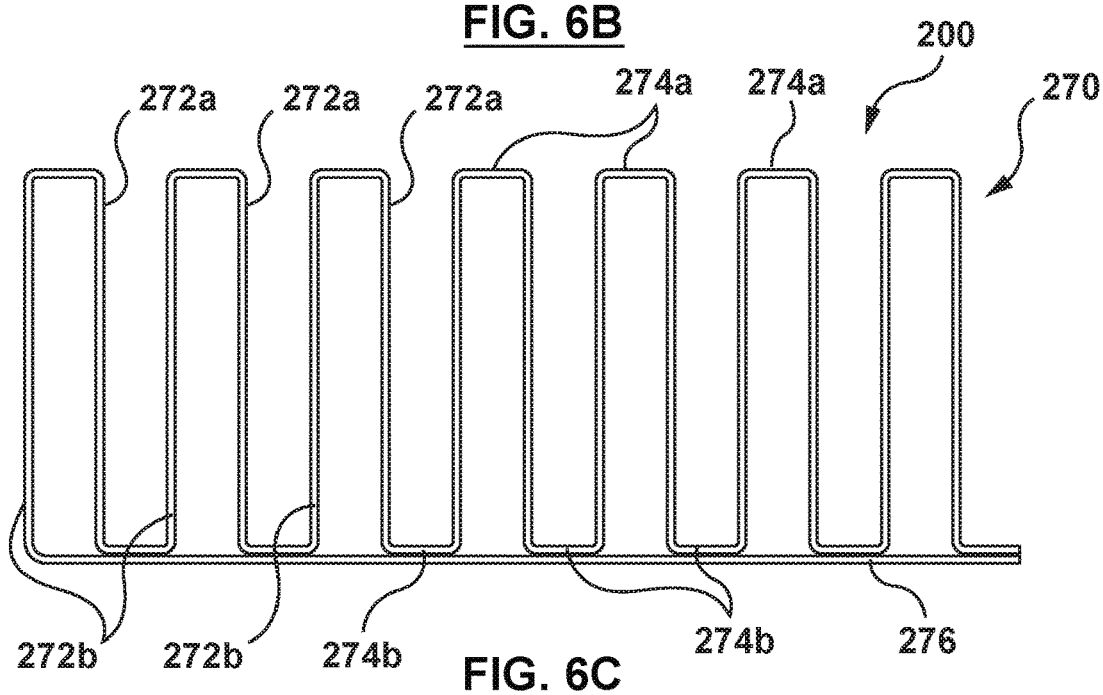
FIG. 6C is a front view of a wire structure of a capsule according to another embodiment hereof, wherein the wire structure is laid out flat for illustrative purposes only.

Modified square pattern 270, as shown in FIG. 6C, includes a series of alternating adjacent straight portions 272a and 272b. Each straight portion 272a is joined to a first adjacent straight portion 272b by a first end portion 274a, and to a second adjacent straight portion 272b by a second end portion 274b. Conversely, each straight portion 272b is joined to two straight portions 272a by first end portion 274a and second end portion 274b. A spine 276 extends along end portions 274b. Spine 276 adds additional tensile rigidity to wire structure 200. End portions 274b adjacent spine 276 may be coupled to spine 276, for example, and not by way of limitation, by welding, adhesives, or other materials suitable for the purposes described herein.

Figure 6D:
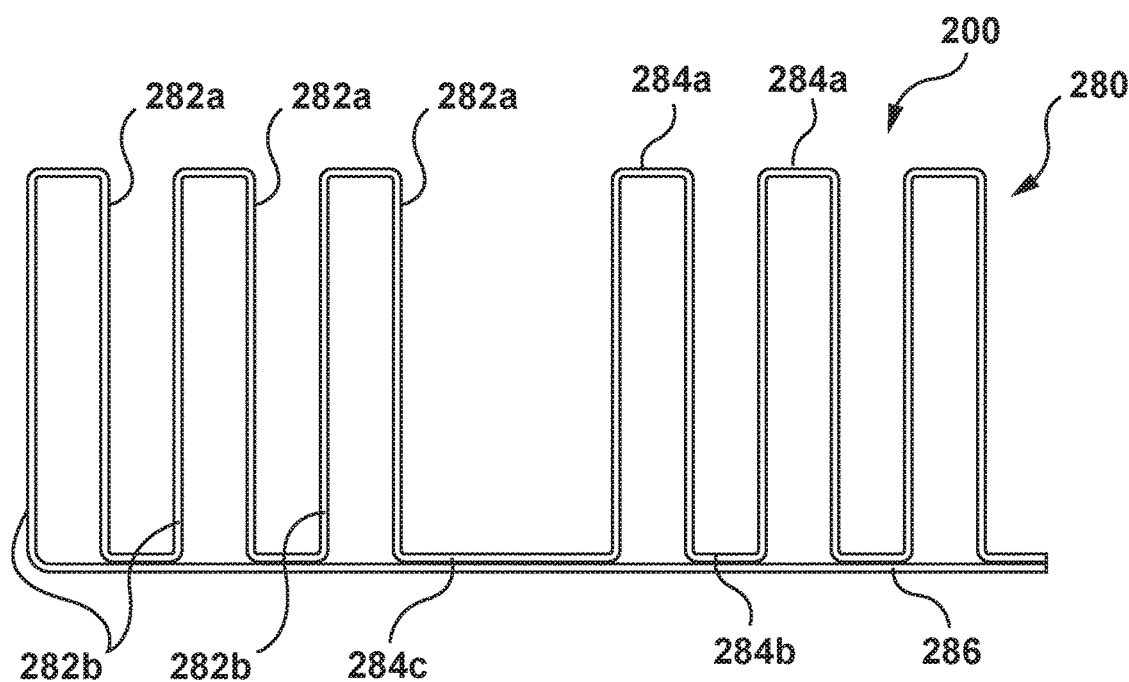
FIG. 6D is a front view of a wire structure of a capsule according to another embodiment hereof, wherein the wire structure is laid out flat for illustrative purposes only.
Figure 6E:
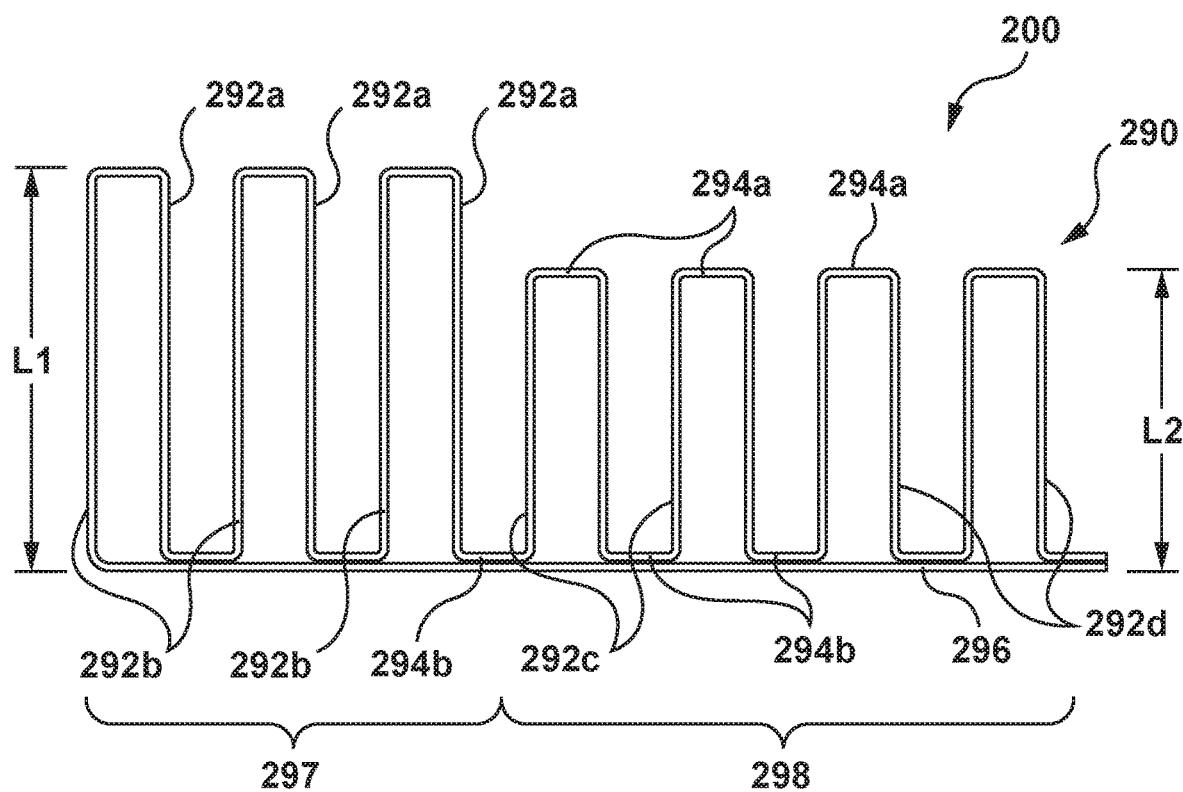
FIG. 6E is a front view of a wire structure of a capsule according to another embodiment hereof, wherein the wire structure is laid out flat for illustrative purposes only.

Modified square pattern 280, as shown in FIG. 6D, includes a series of alternating adjacent straight portions 282a and 282b. Each straight portion 282a is joined to a first adjacent straight portion 282b by a first end portion 284a, and to a second adjacent straight portion 282b by either a second end portion 284b or a preferential bending portion 284c. Conversely, each straight portion 282b is joined to two straight portions 282a by first end portion 284a and either second end portion 284b or preferential bending portion 284c. A spine 286 extends along end portions 284b and preferential bending portion(s) 284c. Preferential bending portion(s) 284c provides increased flexibility to wire structure 200 in the area of preferential bending portion(s) 284c by forming a disjointed or segmented portion of modified square pattern 280 which has no straight portions 282a and 282b. More particularly, in an embodiment, preferential bending portion(s) 284c provides the capsule with flexibility to bend during tracking and delivery. Stated another way, the capsule is permitted to bend at preferential bending portion(s) 284c due to the absence of straight portions 282a and 282b along the length of preferential bending portion(s) 284c. In another embodiment, preferential bending portion(s) 284c provides the capsule with two different expansions zones (i.e., an expansion zone on both sides of the preferential bending portion). Although illustrated at an intermediate portion of wire structure 200, the position of preferential bending portion(s) 284c may vary. In addition, although shown with only one preferential bending portion 284c, wire structure 200 may include a plurality of preferential bending portions 284c spaced apart along the length of spine 286. Spine 286 adds additional tensile rigidity to wire structure 200. End portion 284b and preferential bending portion(s) 284c adjacent spine 286 may be coupled to spine 286, for example, and not by way of limitation, by welding, adhesives, or other materials suitable for the purposes described herein.

Figure 6F:
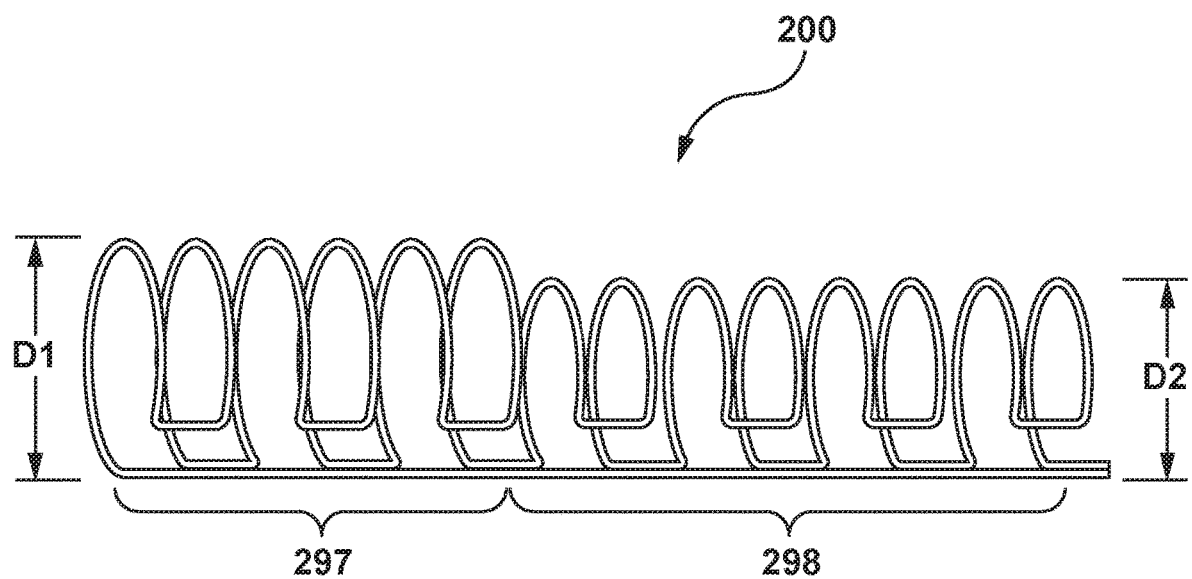
FIG. 6F is a perspective view of the wire structure of FIG. 6E

Modified square pattern 290, as shown in FIG. 6E, includes a series of alternating adjacent straight portions 292a and 292b having a first length L1 along a distal portion 297 of wire structure 200. Modified square pattern 290 further includes a series of alternating adjacent straight portions 292c and 292d having a second length L2 along a proximal portion 298 of wire structure 200. In the embodiment of FIG. 6E, the first length L1 of each straight portion 292a and 292b is greater than the second length L2 of each straight portion 292c and 292d. For distal portion 297 of wire structure 200, each straight portion 292a is joined to a first adjacent straight portion 292b by a first end portion 294a, and to either a second adjacent straight portion 292b, or for the straight portion 292a at a proximal end of distal portion 297 to a second adjacent straight portion 292c, by a second end portion 294b. Conversely, each straight portion 292b is joined to two straight portions 292a by first end portion 294a and second end portion 294b. For the proximal portion 298 of wire structure 200, each straight portion 292c is joined to a first adjacent straight portion 292d by a first end portion 294a, and to either a second adjacent straight portion 282d, or for the straight portion 292c at a distal end of proximal portion 298 to a second adjacent straight portion 292b, by a second end portion 294b. Conversely, each straight portion 292d is joined to two straight portions 292c by first end portion 294a and second end portion 294b. As shown in FIG. 6F, the first length L1 and the second length L2 of straight portions 292a/292b and 292c/292d, respectively, form a stepped profile with a first diameter D1 over the distal portion 297 and a second diameter D2 over the proximal portion 298. First diameter D1 is greater than second diameter D2. The stepped profile of modified square pattern 290 in turn provides the capsule with a stepped profile (not shown), the stepped profile capsule being configured to receive a stented prosthetic heart valve therein as described previously. More specifically, the stepped profile capsule accommodates a stented prosthetic heart valve with larger diameter at a distal portion thereof. For example, a stented prosthetic heart valve may have an additional component at the distal portion thereof that causes the distal portion of the stented prosthetic heart valve to have a larger diameter such as, but not limited to a sealing component configured to prevent paravalvular leakage (PVL) such as a skirt, a cuff, or a sleeve. A sealing component increases the collapsed diameter of the stented prosthetic heart valve over the area of the stented prosthetic heart valve to which it is coupled. Therefore, in the example of FIGS. 6E-6F, the wire structure 200 with an increased first diameter D1 over distal portion 297 accommodates a stented prosthetic heart valve with larger diameter at a distal portion thereof. While the stepped configuration is described herein with a greater diameter over the distal portion 297, this is not meant to be limiting and the greater diameter portion may be disposed over proximal portion 298, or over other portions there between based upon the application. In addition, although shown with a single stepped portion, wire structure 200 may include a plurality of stepped portions spaced apart along the length of a spine 296 to provide a plurality of outer diameters. Further, rather than a single abrupt stepped portion as shown, wire structure 200 may include a plurality of small, adjacent stepped portions that collectively form a single tapered stepped portion. Spine 296 extends along end portions 294b. Spine 296 adds additional tensile rigidity to wire structure 200. End portions 294b adjacent spine 296 may be coupled to spine 296, for example, and not by way of limitation, by welding, adhesives, or other materials suitable for the purposes described herein.

The below discussion refers to sinusoidal portion 250 of wire structure 200, however, square pattern 260 or modified square patterns 270, 280, 290 could also be used for wire structure 200. As shown in FIGS. 6A, 7A, and 7B, along the length of capsule 108, the straight portions of wire structure 200 are curved about a longitudinal axis LA2 into a C-shaped wire structure 200 forming a series of non-continuous circumferential loops. To form the non-continuous circumferential loops, a first loop portion 212 of straight portions 202a and 202b joined by first bent end portion 204a is curved in a first radial direction 210. A second loop portion 222 of straight portions 202a and 202b joined by second bent end portion 204b is curved in a second radial direction 220. First loop portions 212 and second loop portions 222 form a series of alternating non-continuous circumferential loops extending along longitudinal axis LA2. In the collapsed configuration of capsule 108, first loop portions 212 and second loop portions 222 overlap circumferentially as demonstrated by a wire region 214, as shown in FIG. 7B. When capsule 108 is in the collapsed configuration, first loop portions 212 are positioned within second loop portions 222 in wire region such that the second loop portions 222 cover the first loop portions 212. When capsule 108 is in the expanded configuration, first loop portions 212 and second loop portions 222 do not overlap and do not include wire region 214. Stated another way, as capsule 108 transitions between the collapsed configuration and the expanded configuration, circumferential portions 212 and 222 of wire structure 200 expand and collapse, thereby expanding and collapsing wire region 214.

Capsule 108, as shown in FIGS. 8A and 8B, is designed to allow for local expansion and subsequent recoil to retain and release the stented prosthetic heart valve as previously described. While introducing the stented prosthetic heart valve to capsule 108 for delivery to the treatment site within the patient, capsule 108 can transition from the collapsed configuration having outer diameter $OD_c$ (FIG. 8A) to the expanded configuration having outer diameter $OD_e$ (FIG. 8B) to accommodate the stented prosthetic heart valve (not shown). This increase in diameter is accomplished by first loop portions 212 and second loop portions 222 of wire structure 200, as shown in FIGS. 7A and 7B, and inner edge 420 and outer edge 430 of jacket 400, as shown in FIGS. 8A and 8B diverging circumferentially to increase the effective diameter of capsule 108. As capsule 108 increases in diameter, inner fold 320 and outer fold 330 are flattened or stretched apart to allow liner gap portion 340 to span across jacket gap 440. Thus, liner gap portion 340 extends across jacket gap 440 and maintains a circumferentially continuous structure. Upon release of the stented prosthetic heart valve (not shown) at the treatment site within the patient, capsule 108 transitions from the expanded configuration, having outer diameter $OD_e$, to the collapsed configuration, having outer diameter $OD_c$. As previously described, the collapsed configuration, with outer diameter $OD_c$, of capsule 108 is smaller than the inner diameter $ID_a$ of outer stability shaft 110.

Figure 9A:
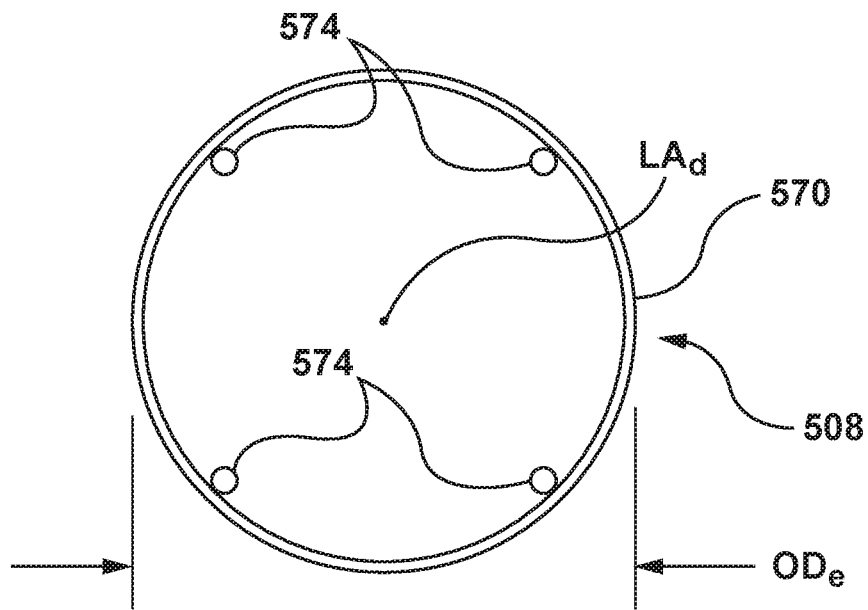
FIG. 9A is an end view of a capsule according to another embodiment hereof, wherein the capsule is shown in an expanded configuration.
Figure 9B:
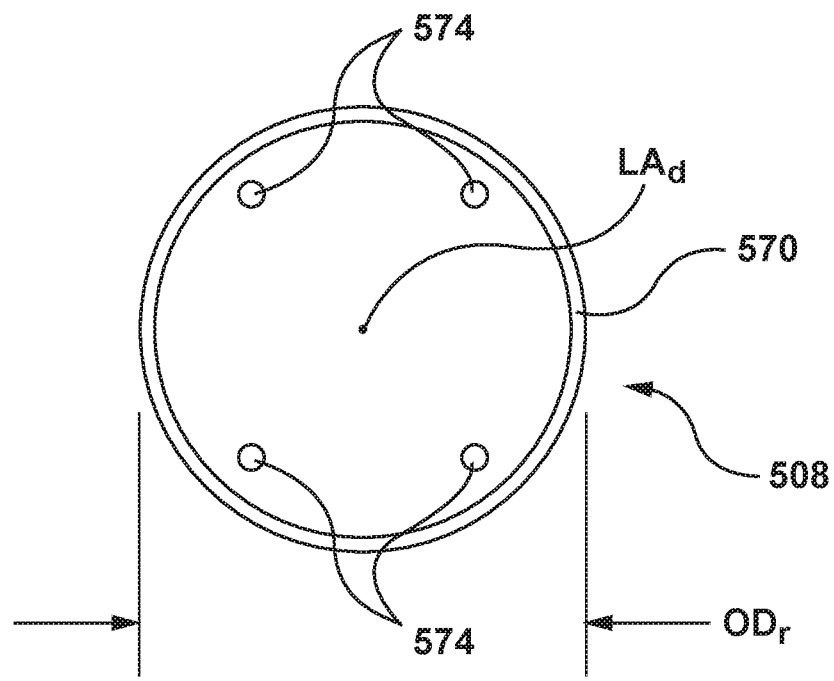
FIG. 9B is an end view of the capsule of FIG. 9A, wherein the capsule is shown in a relaxed or intermediate configuration.
Figure 9C:
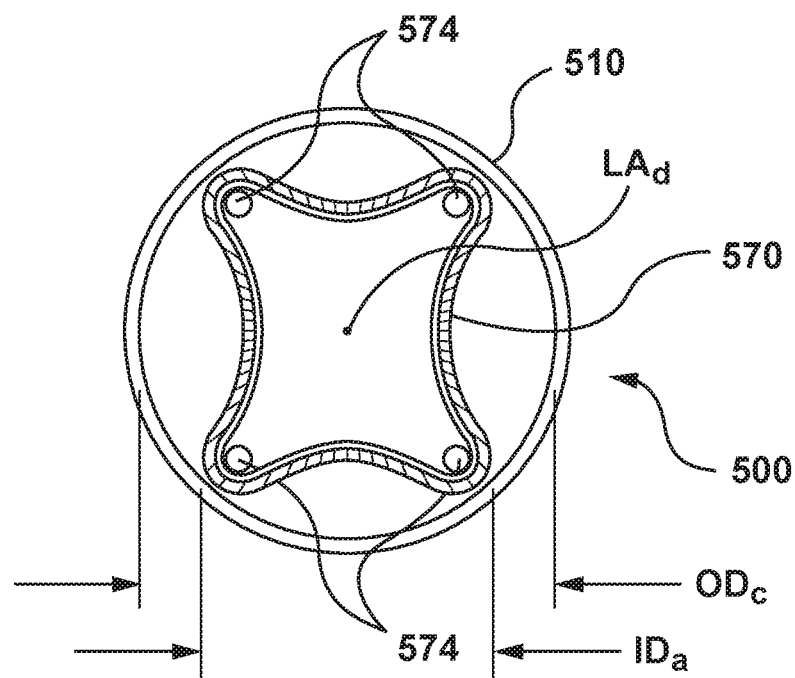
FIG. 9C is an end view of the capsule of FIG. 9A, wherein the capsule is shown in a collapsed or folded configuration.
Figure 10A:
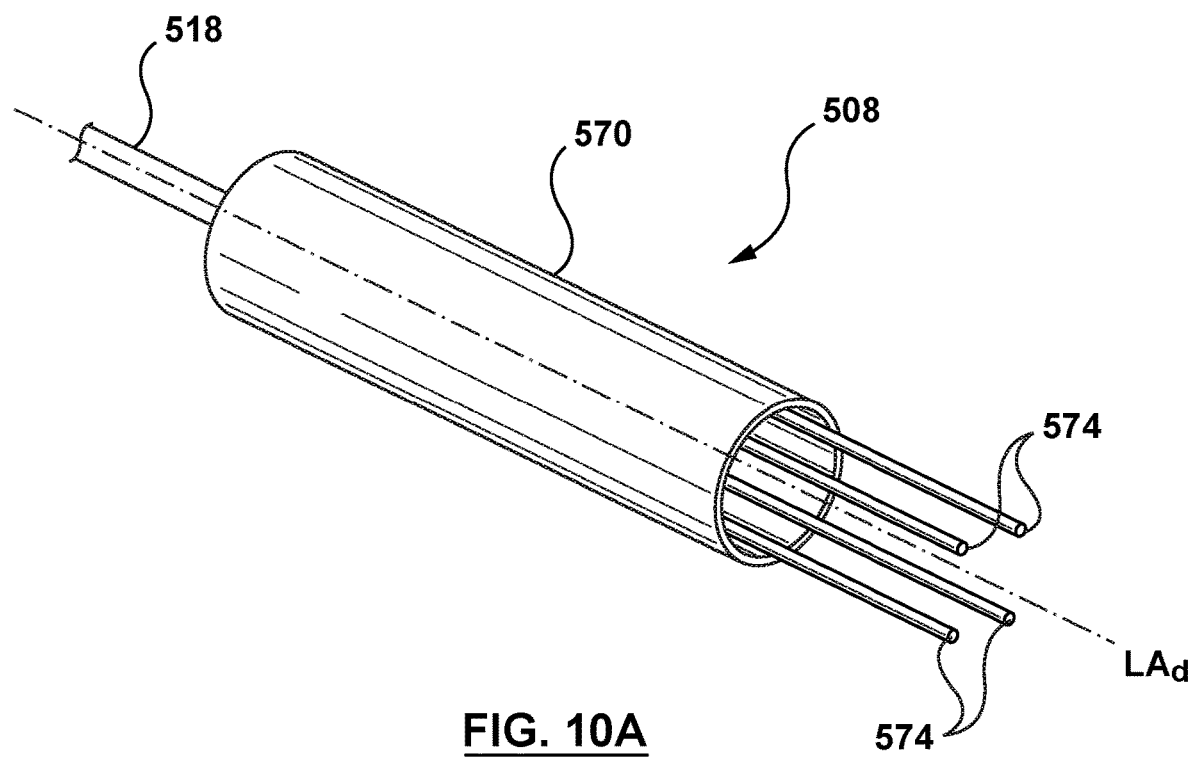
FIG. 10A is perspective and cutaway view of the capsule of FIG. 9A, wherein the capsule is shown in the expanded configuration.
Figure 10B:
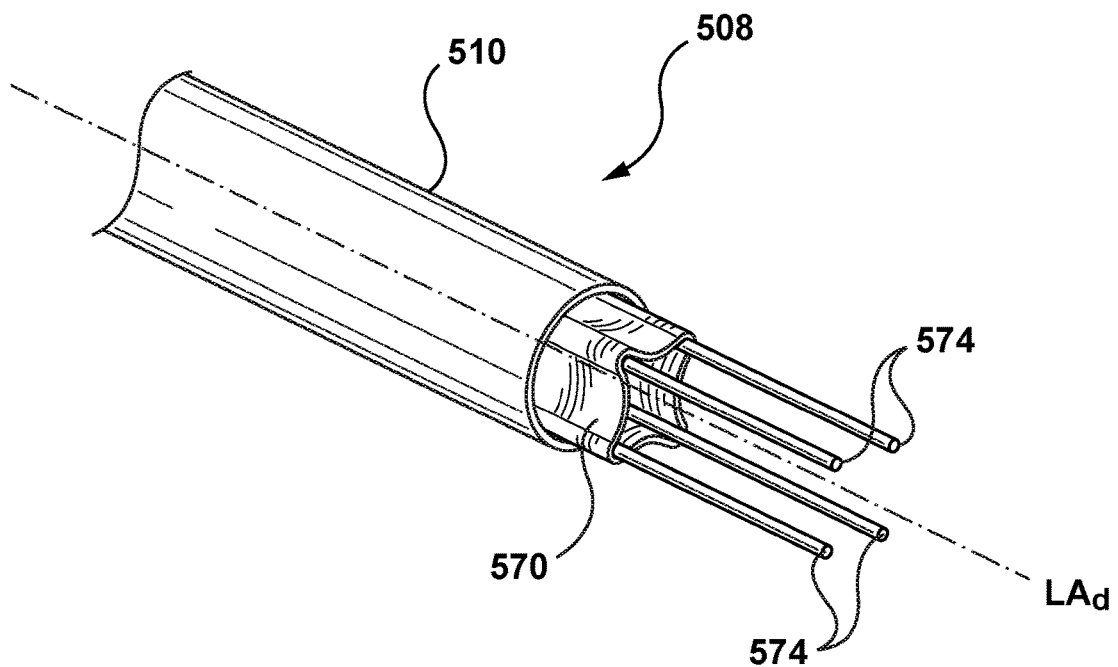
FIG. 10B is a perspective and cutaway view of the capsule of FIG. 9C, wherein the capsule is in the collapsed or folded configuration.

FIGS. 9A-9C and FIGS. 10A-10B illustrate another embodiment of a capsule 508 that is configured to be collapsible upon retraction thereof into an outer stability shaft 510 (not shown in FIGS. 9A-10A) according to an embodiment hereof. Capsule 508 may be utilized in delivery device 500 as described above with respect to delivery device 100. As described above with respect to capsule 108 and proximal shaft 118, capsule 508 is coupled to a proximal shaft 518, shown in FIG. 10A. Capsule 508 includes a generally tubular polymeric structure 570 and a plurality of reinforcing members 574. As best shown in FIGS. 10A and 10B, reinforcing members 574 are axially spaced longitudinal metallic or polymeric wires or rods disposed within and providing compressive strength to capsule 508. Reinforcing members 574 are arranged parallel to longitudinal axis $LA_d$ and coupled to an inner surface of polymeric structure 570. Reinforcing members 574 may be, for example, and not by way of limitation, stainless steel, Nitinol, nylon, polybutylester, or other materials suitable for the purposes described herein. Reinforcing members 574 are coupled to polymeric structure 570, for example, and not by way of limitation, by fusing, welding, adhesive, sutures, or other means suitable for the purposed described herein. While FIGS. 9A-10B show four (4) reinforcing members 574 within polymeric structure 570, this is not meant to limit the design and more or fewer reinforcing members may be employed. Further, reinforcing members 574 may be coupled to an outer surface of polymeric structure 570.

In an embodiment, polymeric structure 570 of capsule 508 is of a shape memory material with a pre-set shape in a relaxed or intermediate configuration of FIG. 9B in which no forces are applied thereto. In the relaxed configuration, capsule 508 has a third outer diameter $OD_r$. Polymeric structure 570 is an elastic structure that allows capsule 508 to stretch or expand to an expanded configuration in which capsule 508 has a first outer diameter $OD_e$ as shown in FIG. 9A, when a stented prosthetic heart valve (not shown) in a radially compressed delivery configuration is disposed therein. Stated another way, when a stented prosthetic heart valve is positioned therein, polymeric structure 570 and reinforcing members 574 attached thereto radially expand to accommodate the stented prosthetic heart valve. The elastic properties of polymeric structure 570 also allow capsule 508 to actively recoil back to third outer diameter $OD_r$ of the relaxed configuration after release of the stented prosthetic heart valve (not shown). First outer diameter $OD_e$ of capsule 508 is greater than third outer diameter $OD_r$ of capsule 508. Further, the elastic properties of polymeric structure 570 also allow capsule 508 to fold to a collapsed or folded configuration in which capsule 508 has a second outer diameter $OD_c$ as shown in FIG. 9C, when capsule 508 is retracted into outer stability shaft 510. Outer stability shaft 510 has an inner diameter $ID_a$. As capsule 508 is retracted into outer stability shaft 510, outer stability shaft 510 imparts compressive radial force on capsule 508, resulting in portions of polymeric structure 570 disposed between adjacent reinforcing members 574 folding inward, towards longitudinal axis $LA_d$ of capsule 508, and reducing capsule 508 to second outer diameter $OD_c$. Polymeric structure 570 may be of a thin-walled polymeric material, for example, and not by way of limitation, polyester, elasthane or any other material suitable for the purpose described herein.

While polymeric structure 570 has been described herein as having a pre-set shape in the relaxed configuration of FIG. 9B with third outer diameter $OD_r$, polymeric structure 570 can alternatively have the pre-set shape in the expanded configuration of FIG. 9A with first outer diameter $OD_e$, the pre-set shape in the collapsed configuration of FIG. 9C with second outer diameter $OD_c$, or any other configuration between the collapsed and expanded configuration based upon the application. When the polymeric structure has a pre-set shape in the expanded configuration, loading forces on the stented prosthetic heart valve are minimized and when the polymeric structure has a pre-set shape in the collapsed configuration, deployment forces on the stented prosthetic heart valve are minimized by reducing the force required to pull the polymeric structure into the outer stability shaft.

Figure 10C:
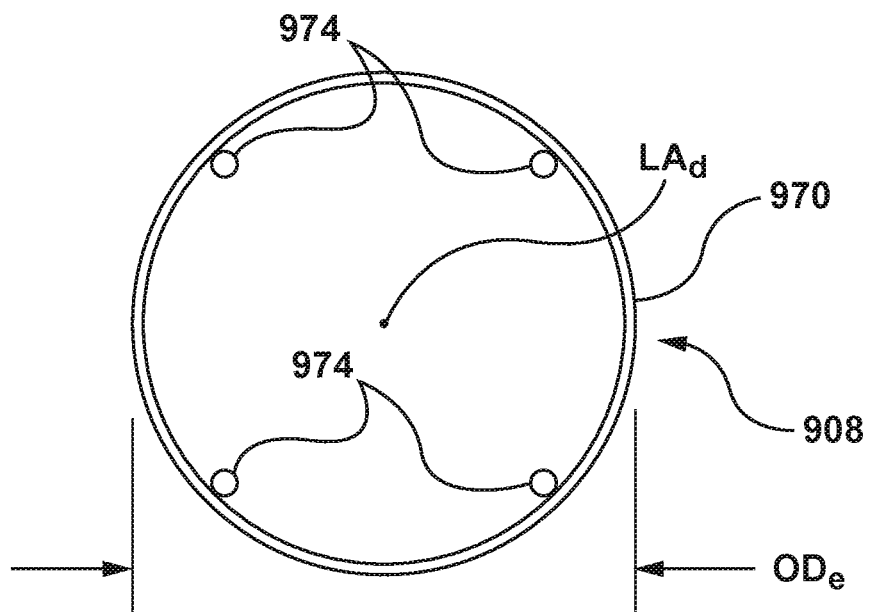
FIG. 10C is an end view of a capsule according to another embodiment hereof, wherein the capsule is shown in an expanded configuration.
Figure 10D:
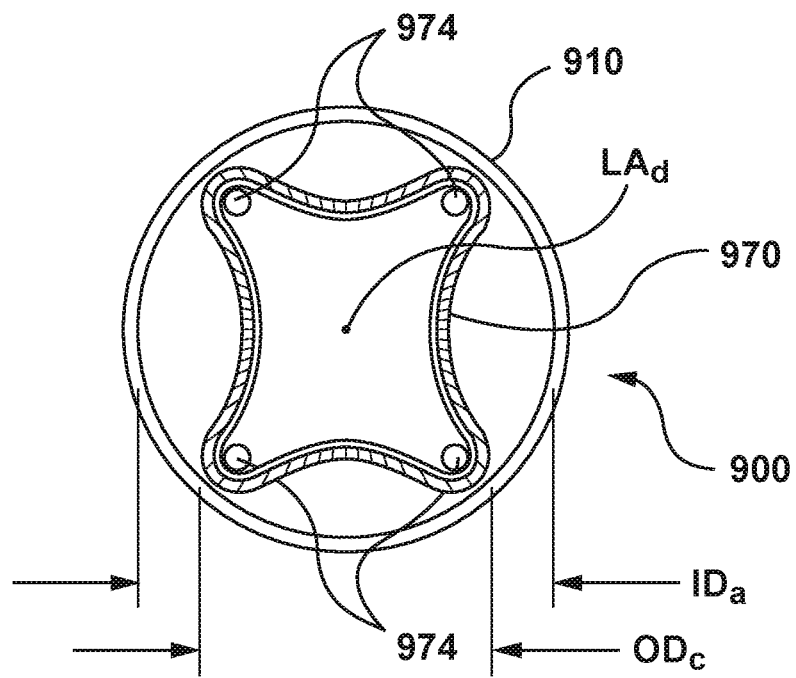
FIG. 10D is an end view of the capsule of FIG. 10C, wherein the capsule is shown in a collapsed or folded configuration.

In another embodiment, as described above with respect to delivery device 500, capsule 508, and polymeric structure 570, polymeric structure 970 of capsule 908 of delivery device 900 is of a shape memory material with a pre-set shape in an expanded configuration of FIG. 10C in which no forces are applied thereto. In the expanded configuration, capsule 908 has a first outer diameter $OD_e$. Polymeric structure 970 is a non-elastic structure that allows capsule 908 to impart compressive radial forces on a stented prosthetic heart valve (not shown) in a radially compressed delivery configuration disposed therein. Polymeric structure 970 allows capsule 908 to fold to a collapsed or folded configuration in which capsule 908 has a second outer diameter $OD_c$ as shown in FIG. 10D, when capsule 908 is retracted into outer stability shaft 910. Outer stability shaft 910 has an inner diameter $ID_a$. As capsule 908 is retracted into outer stability shaft 910, outer stability shaft 910 imparts compressive radial force on capsule 908, resulting in portions of polymeric structure 970 disposed between adjacent reinforcing members 974 folding inward, towards longitudinal axis $LA_d$ of capsule 908, and reducing capsule 908 to second outer diameter $OD_c$. Polymeric structure 970 may be of a thin-walled polymeric material, for example, and not by way of limitation, polypropylene or any other materials suitable for the purpose described herein.

Figure 11A:
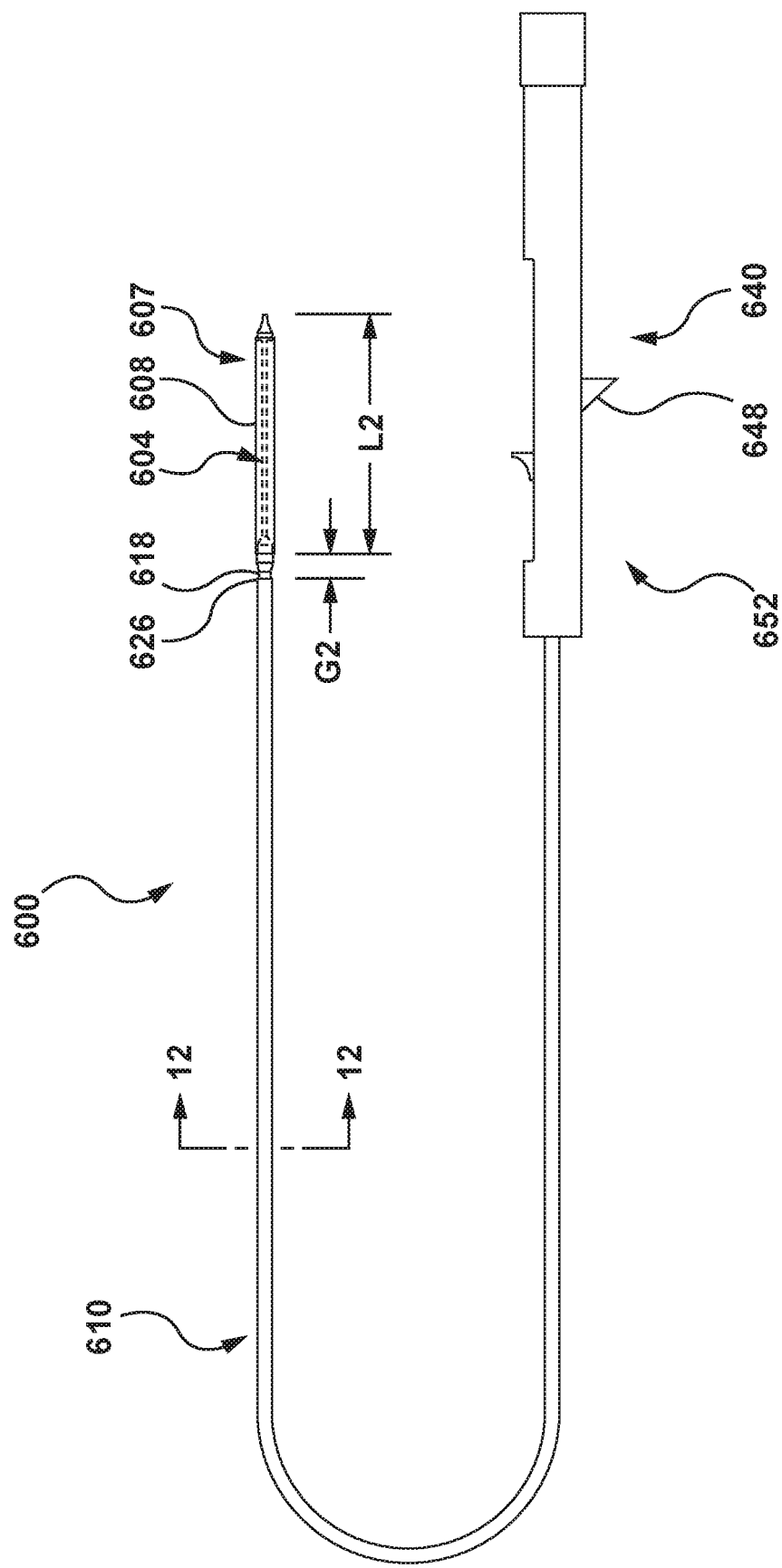
FIG. 11A is a side illustration of another embodiment of a delivery device of the present disclosure, with a steering mechanism, and a capsule in an expanded configuration.
Figure 11B:
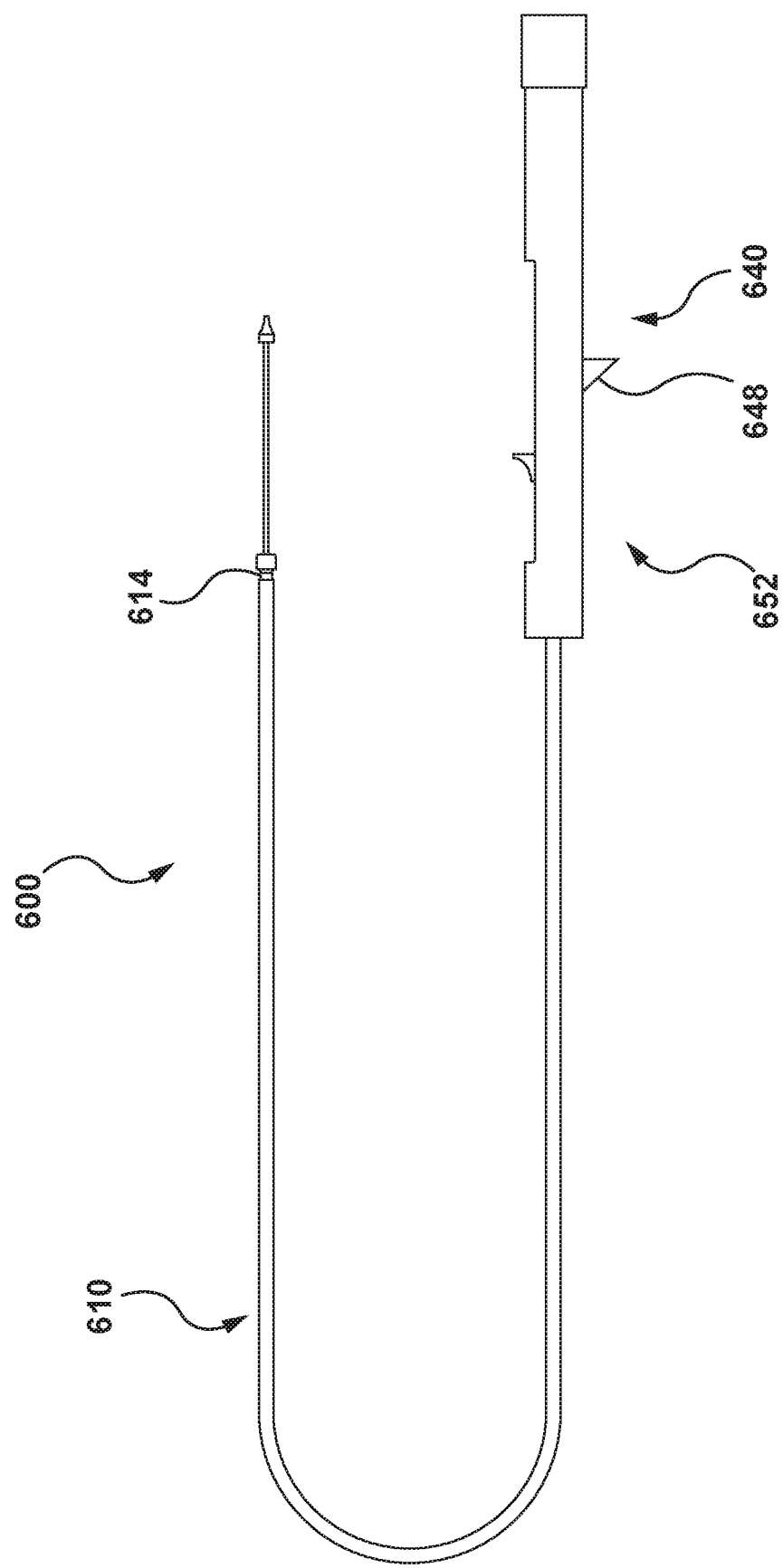
FIG. 11B is a side illustration of the delivery device of FIG. 11A with the capsule in a collapsed configuration.
Figure 11C:
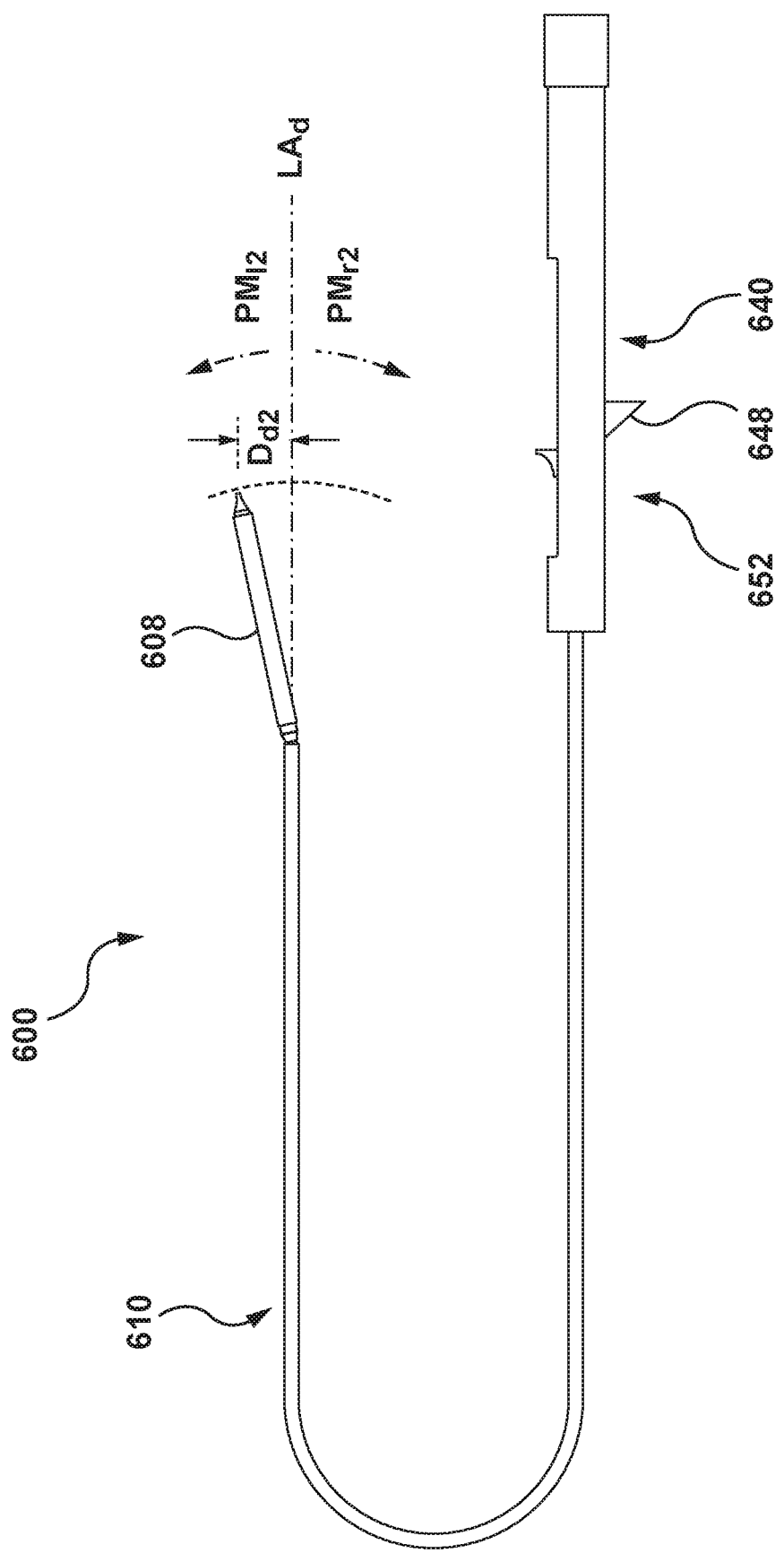
FIG. 11C is a side illustration of the delivery device of FIG. 11A with the capsule in the expanded configuration, showing the delivery device bending in one plane and a deflection distance of the capsule.
Figure 12:
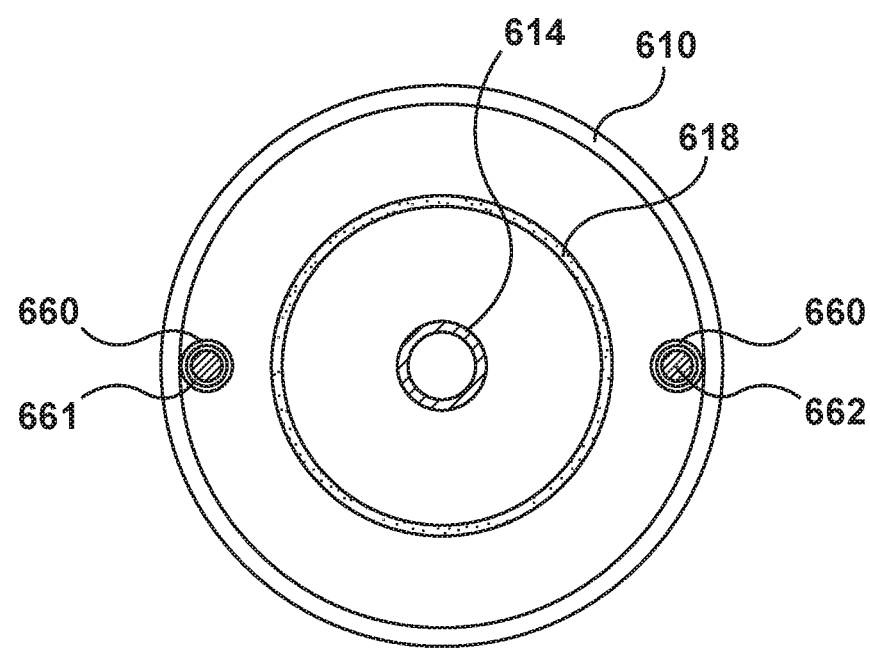
FIG. 12 is a cross-sectional view of a steering mechanism of FIG. 11A taken along line 12-12 of FIG. 11A.

In any embodiment hereof, an outer stability shaft of a delivery device may be modified to include a steering mechanism to enable the centering of a delivery device within a valve annulus. For example, FIGS. 11-12 illustrate a steering mechanism 652 coupled to an outer stability shaft 610 of delivery device 600. Delivery device 600 is similar to delivery device 100 as previously described herein. Delivery device 600 includes a capsule assembly 607, outer stability assembly 610, and inner shaft assembly 614, as shown in FIG. 11A. Similar to capsule assembly 107, capsule assembly 607 includes a capsule 608 and a proximal shaft 618 as previously described. Steering mechanism 652 of delivery device 600 includes a steering actuator 648 at a handle 640, as shown in FIG. 11A, and a plurality of pull cable shafts 660 defining a plurality of lumen 661 with a plurality of pull cables 662 disposed therein, as shown in FIG. 12. Pull cables 662 include a proximal end (not shown) coupled to steering actuator 648 of handle 640 and a distal end (not shown) coupled to a distal end 626 of outer stability shaft 610, and disposed within respective lumens 661, therein. Cable shafts 660 may be connected to an inner surface of outer stability shaft 610 for example, and not by way of limitation, by fusing, welding, adhesive, sutures, or other means suitable for the purposed described herein. Proximal ends (not shown) of pull cables 662 may be connected to steering actuator 648 of handle 640 for example, and not by way of limitation, by fusing, welding, adhesive, sutures, or other means suitable for the purposed described herein. Distal ends (not shown) of pull cables 662 may be connected to distal end 626 of outer stability shaft 610 for example, and not by way of limitation, by welding, adhesive, sutures, or other means suitable for the purposed described herein. While the steering embodiment of FIGS. 11-12 show pull cable shafts 660 and respective pull cables 662 disposed directly across from each other, or at 180 degrees from each other on an interior surface of outer shaft 610, this is not meant to be limiting and other configurations of pull shafts 660 and respective pull cables 662 are envisioned. For example, and not by way of limitation, pull shafts 660 and their respective pull cables 662 may be disposed at 90 degrees from each other such that outer shaft 610 may be steered in two (2) planes.

Figure 1A:
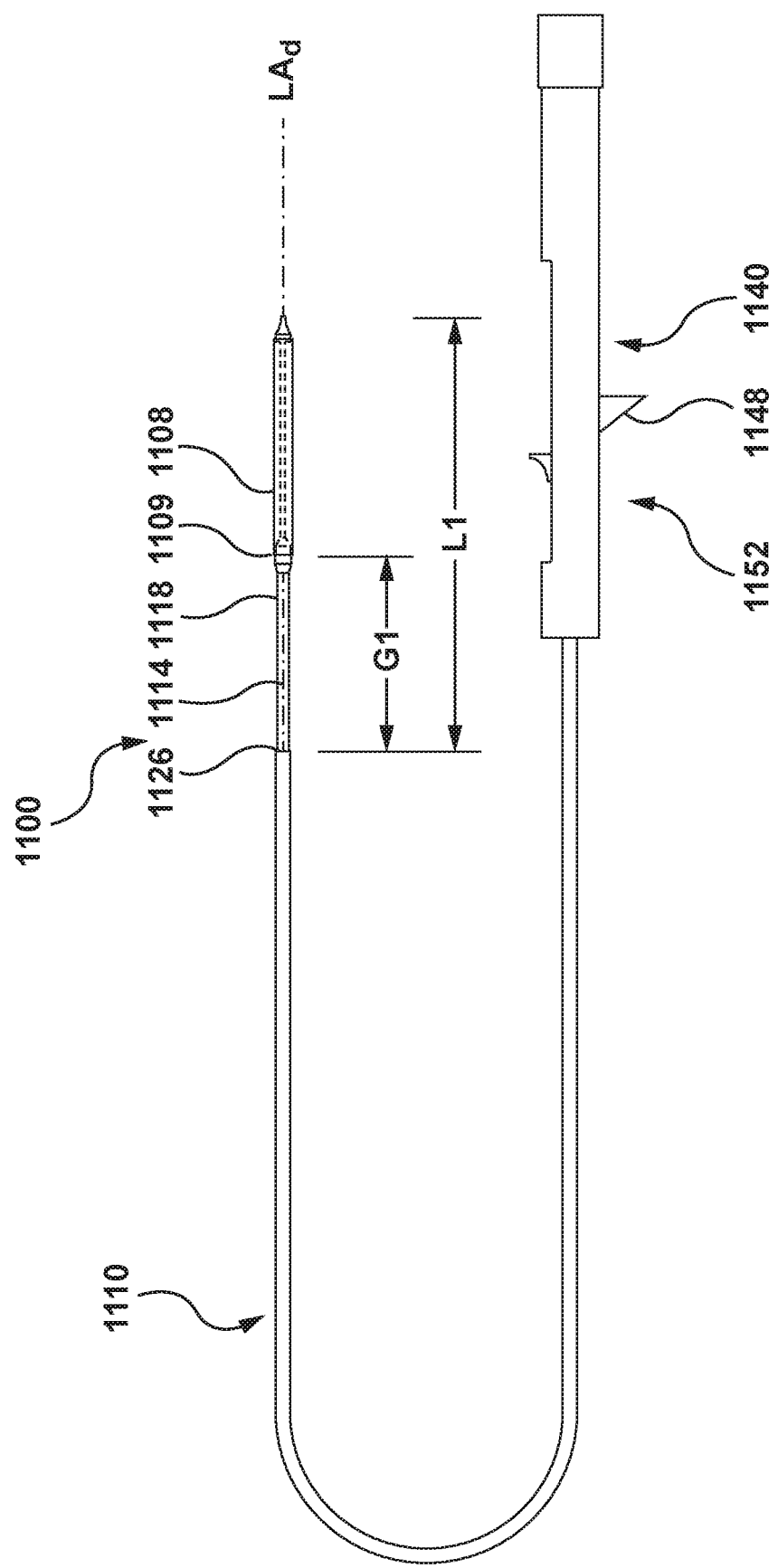
FIG. 1A is a simplified illustration of a prior art transcatheter delivery device in a delivery configuration.
Figure 1B:
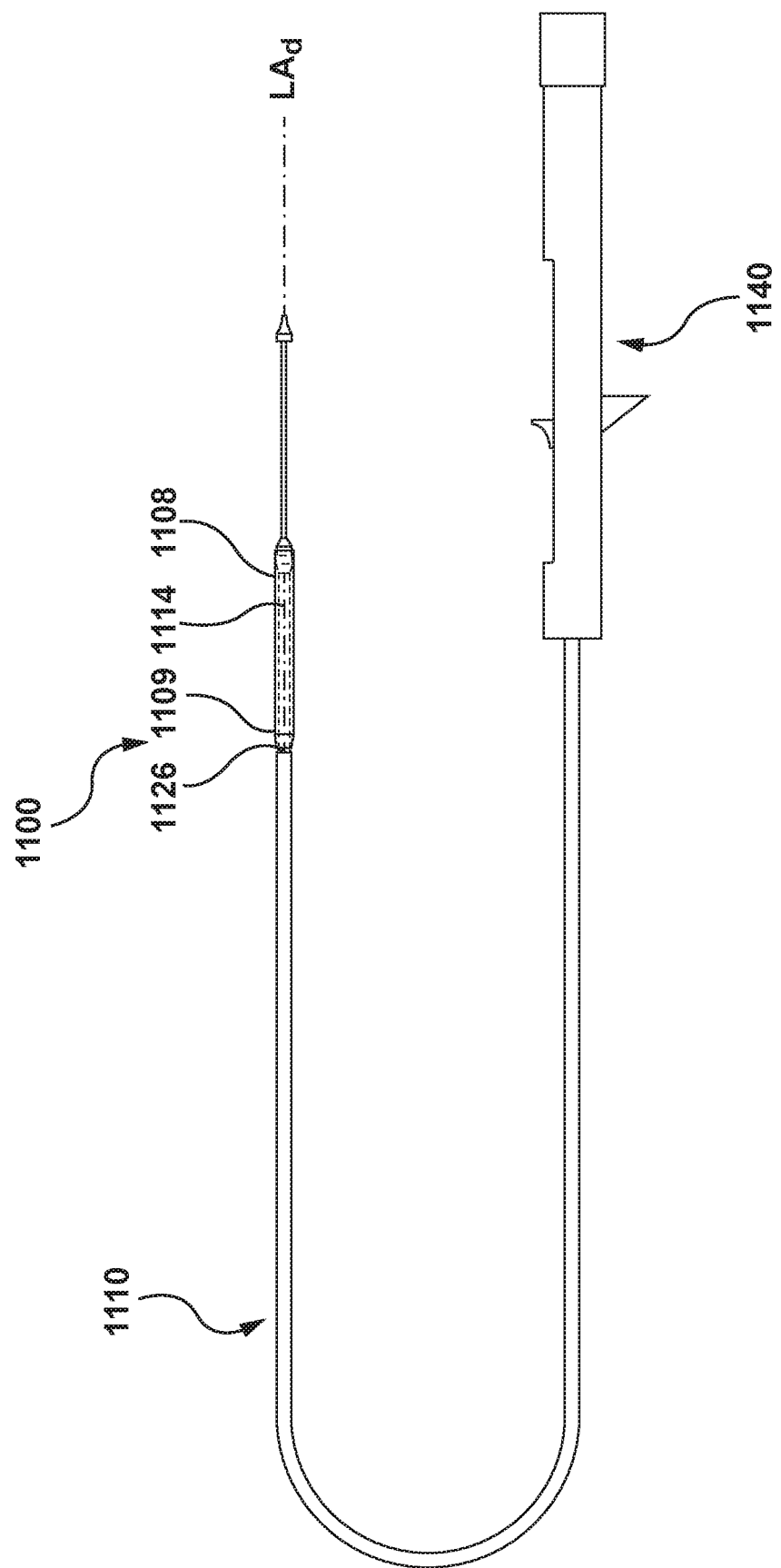
FIG. 1B is a simplified illustration of a prior art transcatheter delivery device with a retracted capsule assembly.
Figure 1C:
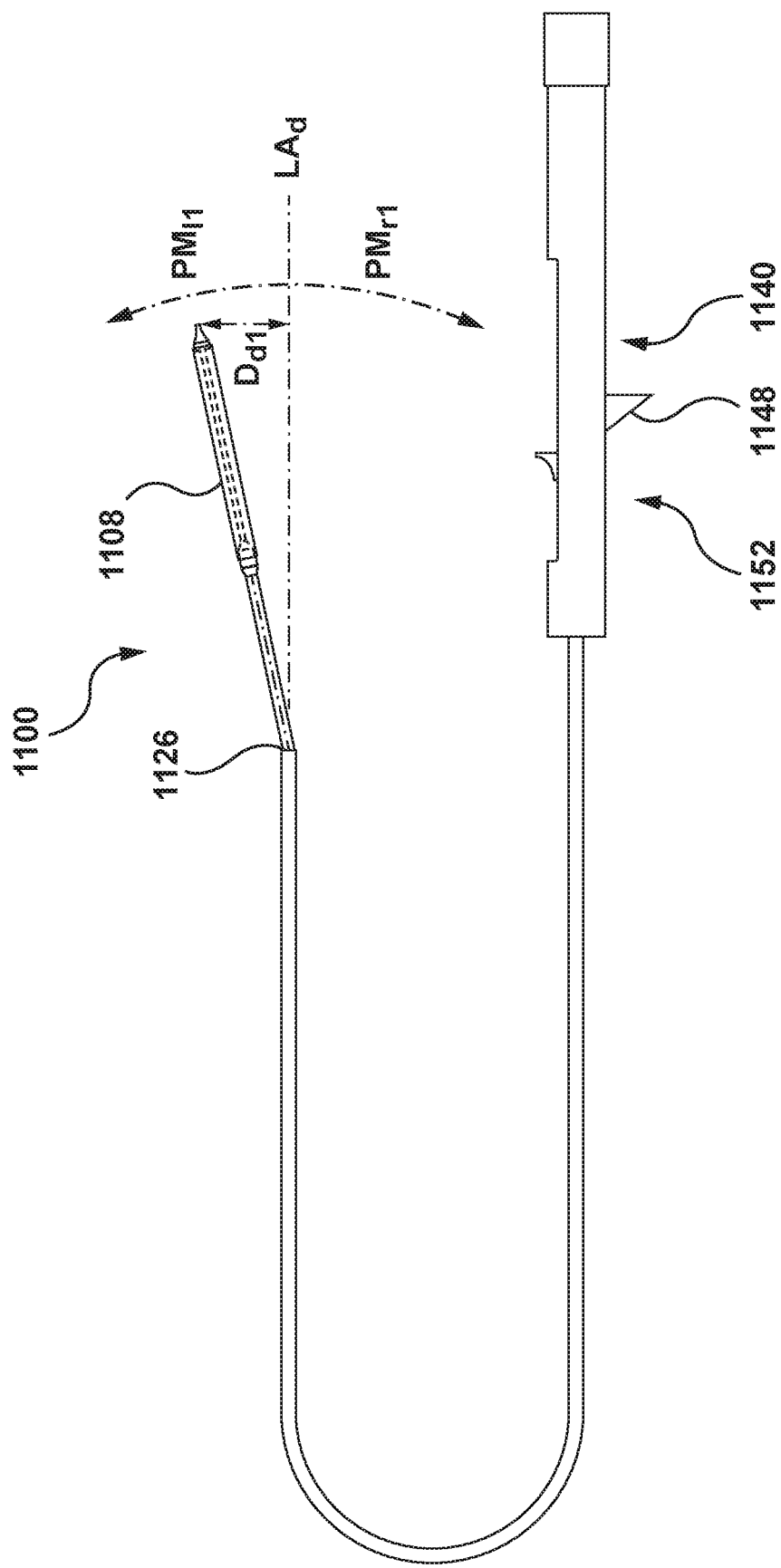
FIG. 1C is a simplified illustration of a prior art transcatheter delivery device showing planer movement of the capsule.

Delivery device 600 includes a capsule 608 configured to be collapsed on retraction thereof into outer stability shaft 610. As capsule 608 is configured to be collapsed on retraction thereof into outer stability shaft 610, capsule 608 is disposed directly adjacent to distal end 626 of outer stability shaft 610, as shown in FIG. 11A, with the capsule in an expanded configuration and FIG. 11B, with capsule 608 in a collapsed configuration. Capsule 608 being disposed directly adjacent to distal end 626 of outer stability shaft 610 minimizes a gap distance G2, thus minimizing a lever arm L2. Steering actuator 648 of delivery device 600 may be user manipulated left or right relative to a longitudinal axis $LA_d$ of handle 640. Steering mechanism 652 is configured such that user manipulation left or right of steering actuator 648 is translated though pull cables 662, as shown in FIG. 12, to a user definable single planar movement $PM_{l2}$ or $PM_{r2}$ relative to longitudinal axis $LA_d$, and a deflection distance $D_{d2}$ of distal end 626 of outer shaft 610, as shown in FIG. 11C, Since capsule 608 is disposed directly adjacent to distal end 626 of outer stability shaft 610, a minimized lever arm L2 is reduced or shortened relative to lever arm L1 discussed with respect to FIG. 1A. The minimized lever arm L2 results in improved steering accuracy and smaller planer movement $PM_{l2}$ and $PM_{r2}$ and smaller deflection distance $D_{d2}$ of capsule 608 and a stented prosthetic heart valve therein, relative to the planer movements and deflection distance discussed with respect to FIG. 1A. Stated another way, with collapsible capsule 608 disposed directly adjacent to distal end 626 of outer stability shaft 610, small movements of steering actuator 648, combined with the minimized length of lever arm L2 resulting thereof, translate to relatively small planar movement $PM_{l2}$ or $PM_{r2}$ and small, precise deflection distance $D_{d2}$ of capsule 608 and the stented prosthetic heart valve retained therein.

Figure 13A:
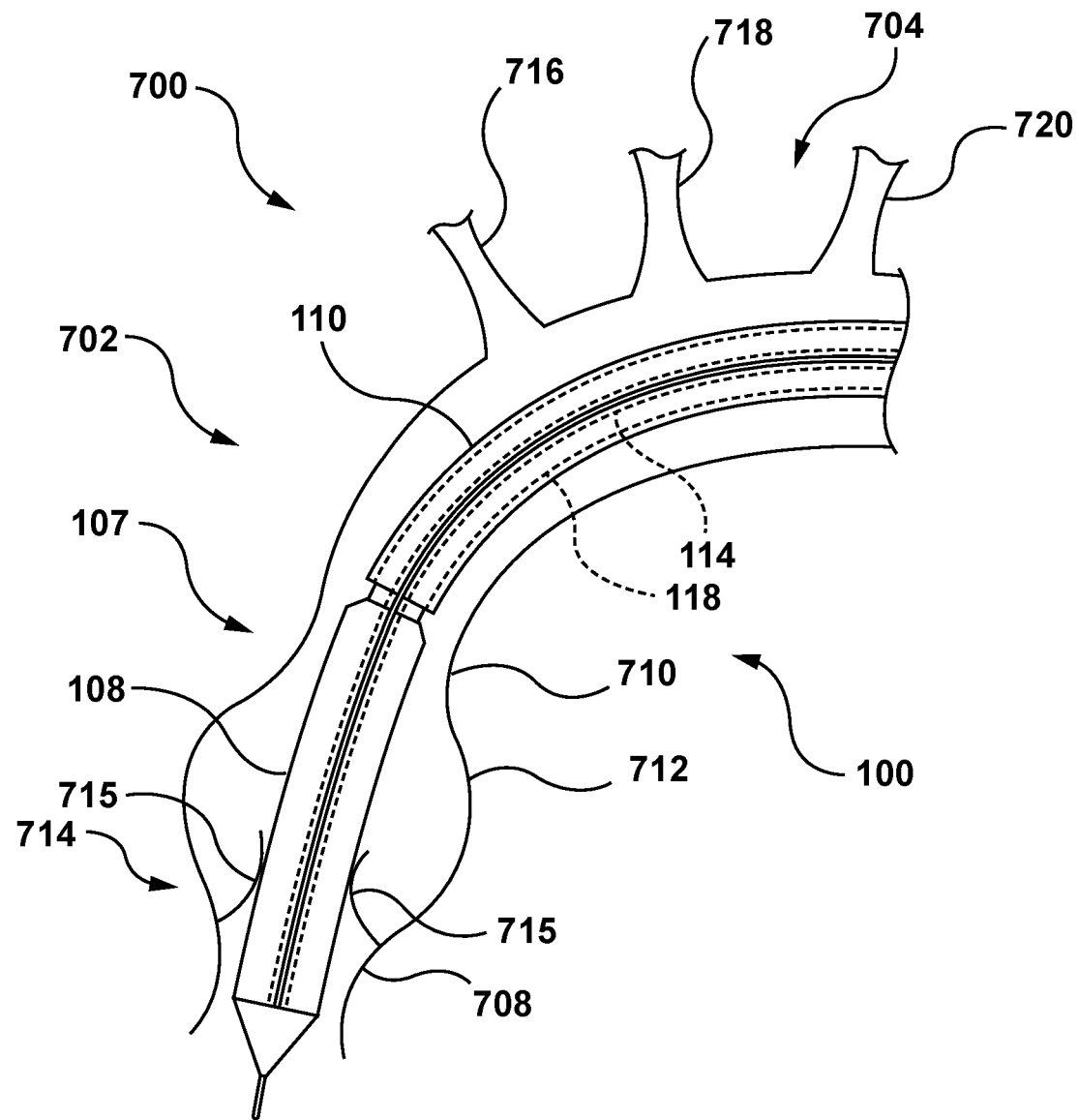
FIGS. 13A is a simplified illustration of the delivery device of FIG. 2A, wherein the delivery device is in a delivery configuration and positioned within an aorta.
Figure 13B:
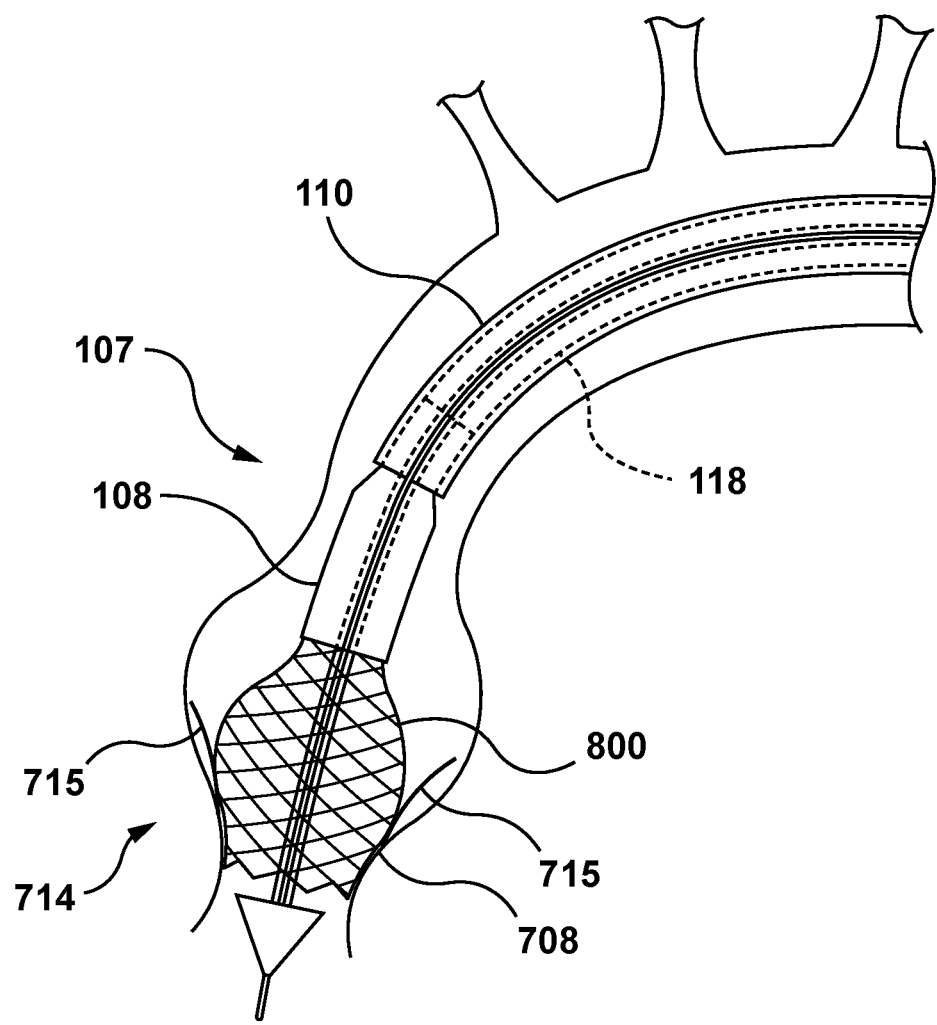
FIG. 13B is a simplified illustration of the delivery device of FIG. 2A and an expanding stented prosthetic heart valve.
Figure 13C:
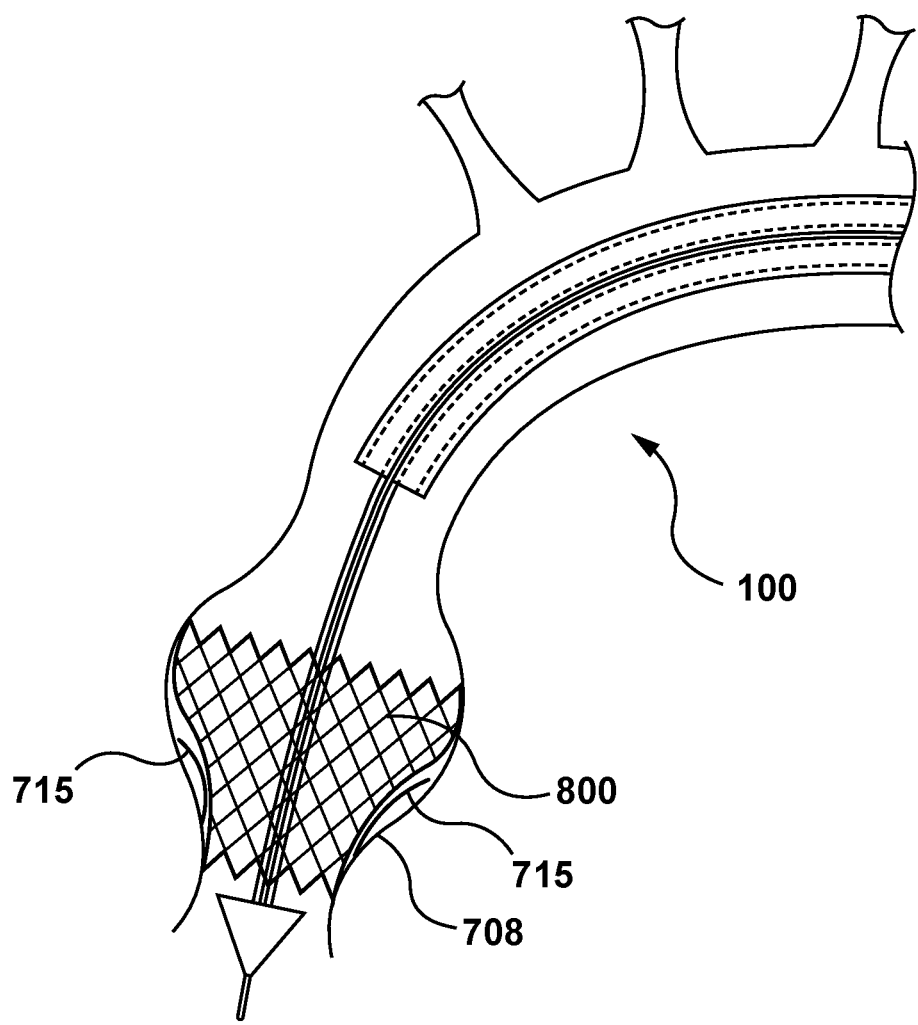
FIG. 13C is a simplified illustration of the delivery device of FIG. 2A and the stented prosthetic heart valve in a radially expanded deployed configuration.

A method of manipulating a delivery device with a stented prosthetic heart valve loaded therein, in accordance with an embodiment hereof, is schematically represented in FIGS. 13A-13C. Using established percutaneous transcatheter delivery procedures, delivery device 100 is introduced into a patient's vasculature and positioned at a treatment site of a damaged or diseased native valve, which in this embodiment is a native aortic valve 714. Delivery device 100 includes a handle (not shown), outer stability shaft 110, proximal shaft 118, inner shaft 114, and capsule assembly 107 as previously described. Delivery device 100 is advanced through the aorta 700 (including the aortic arch 704 (passing the innominate or brachiocephalic artery 716, the left common carotid artery 718, and the left subclavian artery 720, ascending aorta 702, sinotubular junction 710, aortic sinuses 712) to a valve annulus 708 and between native valve leaflets 715 of the damaged or disease native aortic valve 714, as shown in FIG. 13A. Although described herein with delivery device 100, it will be apparent to one of ordinary skill that methods described herein may utilize a delivery device according to any embodiment described herein. In FIG. 13A, capsule 108 of capsule assembly 107 is in the expanded configuration and is positioned over a stented prosthetic heart valve 800 (obscured from view in FIG. 13A).

Next, actuator mechanism 144 of handle 140 (not shown on FIGS. 13A-13C) is operated proximally to retract capsule assembly 107. In particular, proximal shaft 118 and capsule 108 are moved proximally to withdraw capsule 108 from its position surrounding stented prosthetic heart valve 800, and retract capsule 108 into lumen 128 (not shown on FIGS. 13A-13C) of outer stability shaft 110, as shown in FIG. 13B. As capsule 108 is retracted proximally, capsule 108 transitions from the expanded configuration with outer diameter $OD_e$ to the collapsed configuration with outer diameter $OD_c$. As previously described herein, outer diameter $OD_c$ of capsule 108 is smaller than outer diameter $OD_e$ of capsule 108 and is also smaller than inner diameter $ID_a$ of outer stability shaft 110. Of note, as stented prosthetic heart valve 800 expands, it traps native leaflets 715 against the wall of valve annulus 708.

Once stented prosthetic heart valve 800 is fully deployed and in the radially expanded deployed configuration (with native valve leaflets 715 disposed between the wall of valve annulus 708 and an outer surface of stented prosthetic heart valve 800), as shown in FIG. 13C, delivery device 100 may be retracted and removed from the patient's vasculature using established procedures.

Figure 14A:
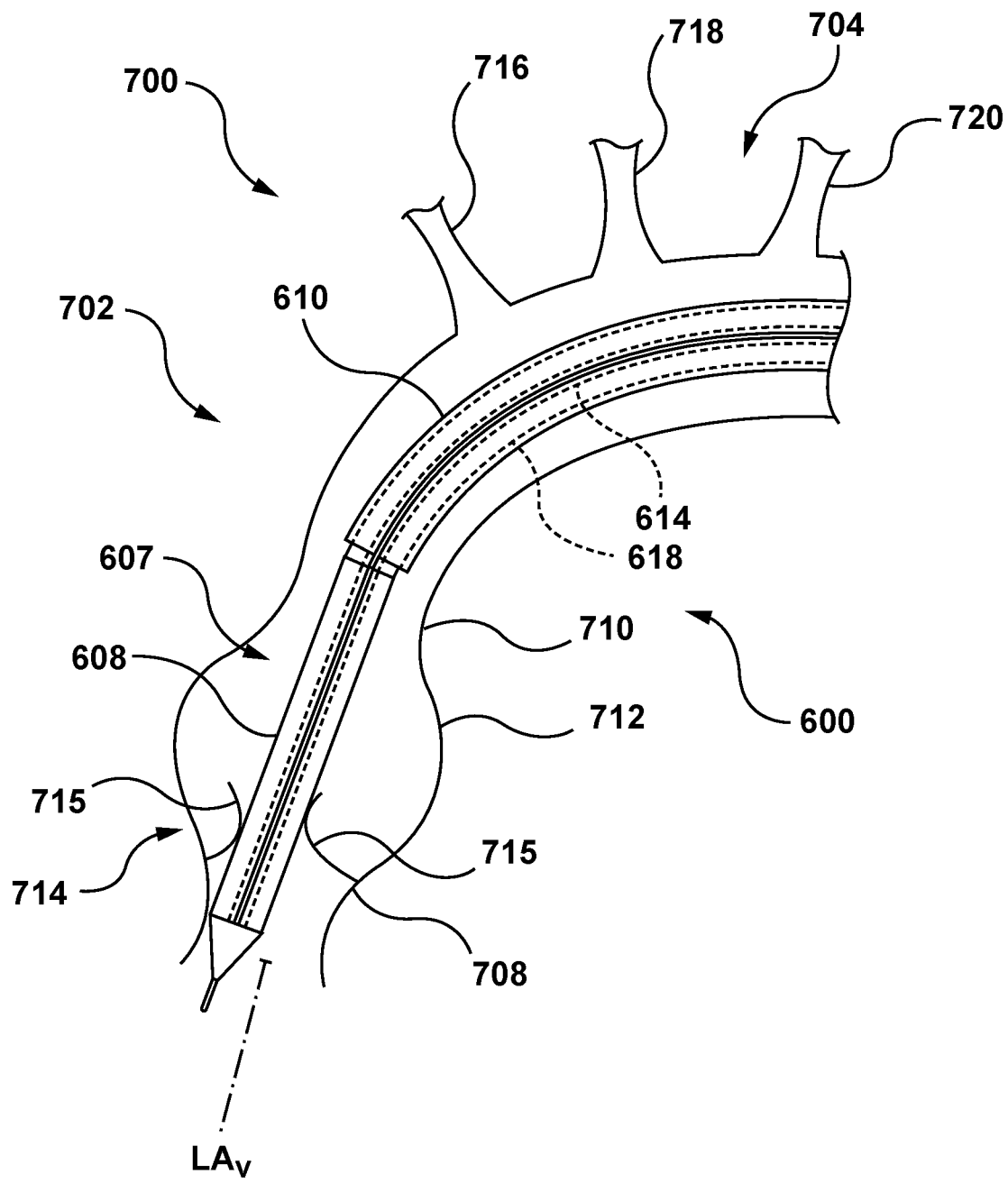
FIG. 14A is a simplified illustration of the delivery device of FIG. 2A, wherein the delivery device is in a delivery configuration and is not centered on a longitudinal axis of a valve annulus.

Another method of manipulating a delivery device with a stented prosthetic heart valve loaded therein, in accordance with an embodiment hereof, is schematically represented in FIGS. 14A-14E. The method steps of FIGS. 14A-14E are described with respect to delivery device 600 that includes steering mechanism 652 as described above. Using established percutaneous transcatheter delivery procedures, delivery device 600 is introduced into a patient's vasculature and positioned longitudinally at the site of a damaged or diseased native valve, which in this embodiment is the native aortic valve 714. Delivery device 600 includes a handle (not shown), outer stability shaft 610, proximal shaft 618, inner shaft 614, steering mechanism 652 (not shown in FIGS. 14A-14E), and capsule assembly 607 as previously described. Delivery device 600 is advanced through the aorta 700 (including the aortic arch 704 (passing the innominate or brachiocephalic artery 716, the left common carotid artery 718, and the left subclavian artery 720, ascending aorta 702, sinotubular junction 710, aortic sinuses 712) to valve annulus 708 and between native valve leaflets 715 of the damaged or disease native aortic valve 714, as shown in FIG. 14A. In FIG. 14A, capsule 608 of capsule assembly 607 is in the expanded configuration and is positioned over stented prosthetic heart valve 800 (obscured from view in FIG. 14A). Capsule 608 is not centered on longitudinal axis $LA_v$ of valve annulus 708.

Figure 14B:
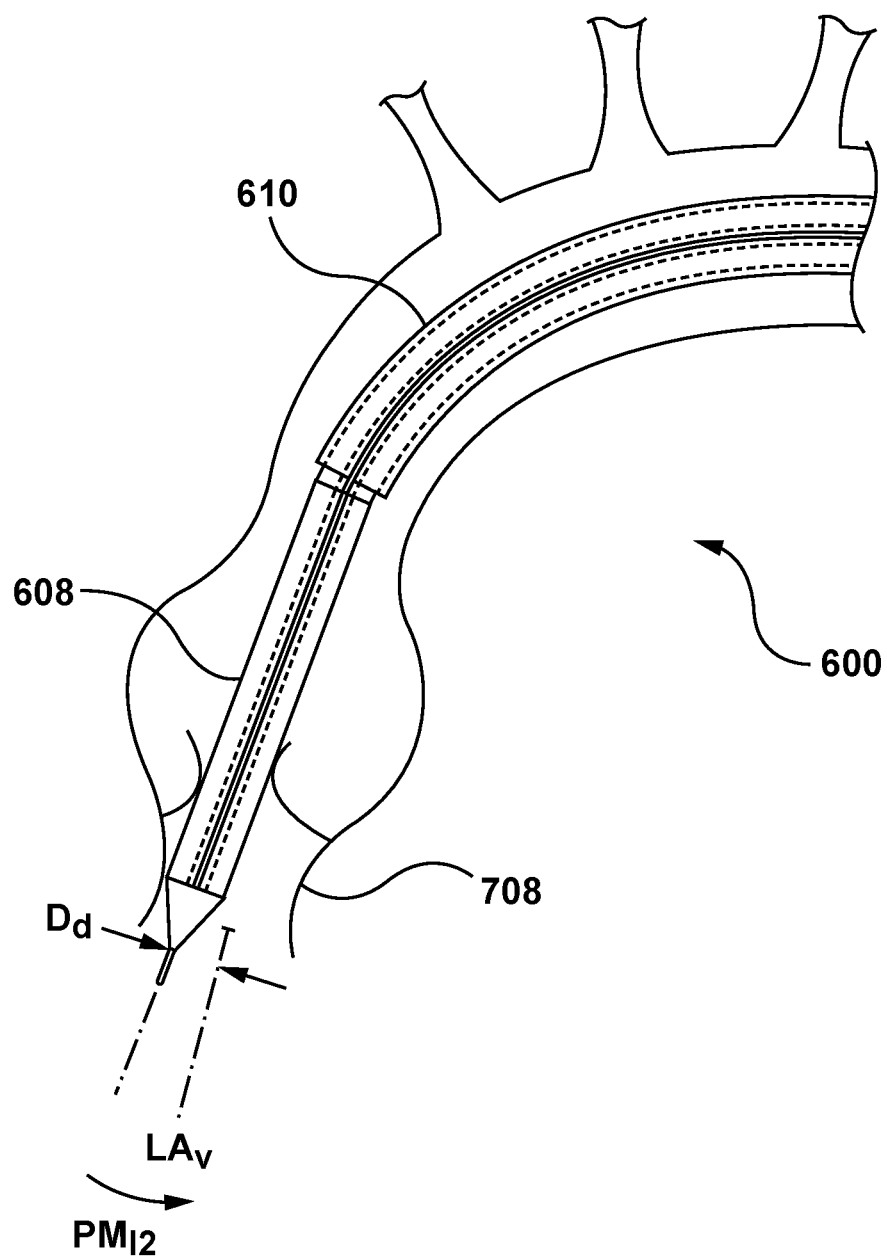
FIG. 14B is a simplified illustration of the delivery device of FIG. 2A, wherein the delivery device is adjusted to align with the longitudinal axis of the valve annulus.

Next the centered position of capsule 608 relative to longitudinal axis $LA_v$ of valve annulus 708 may be adjusted using steering mechanism 652 (not shown in FIGS. 14A-14E) coupled to outer stability shaft 610. Steering actuator 648 (not shown) of steering mechanism 652 (not shown) of delivery device 600 is manipulated by the user to move capsule 608 in direction $PM_{r2}$ the deflection distance $D_{d2}$ to center capsule 608 on longitudinal axis $LA_v$ at the desired deployment location, as shown in FIG. 14B. With capsule 608 being collapsible and disposed directly adjacent to distal end 626 (not shown) of outer stability shaft 610 as previously described rather than spaced apart therefrom, small movements of steering actuator (not shown), translate to relatively small planar movement $PM_{r2}$ and relatively small, precise deflection distance $D_{d2}$ of capsule 608 and stented prosthetic heart valve 800 (obscured in FIG. 14B) retained therein. Determination of desired deployment location and centering may be based upon known methods, for example, and not by way of limitation, such as sonography and radiopaque markers.

Figure 14C:
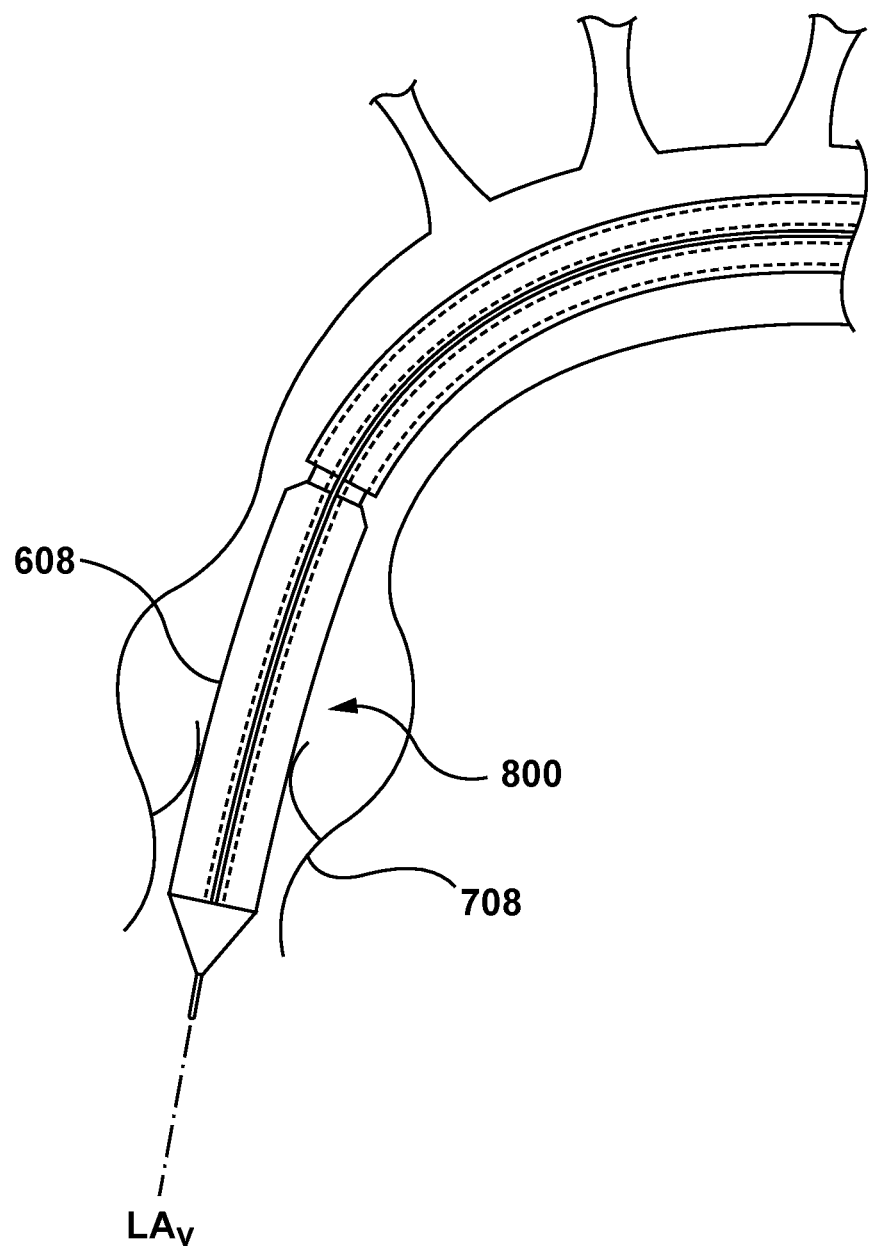
FIG. 14C is a simplified illustration of the delivery device of FIG. 2A, wherein the delivery device is centered on the longitudinal axis of the valve annulus.
Figure 14D:
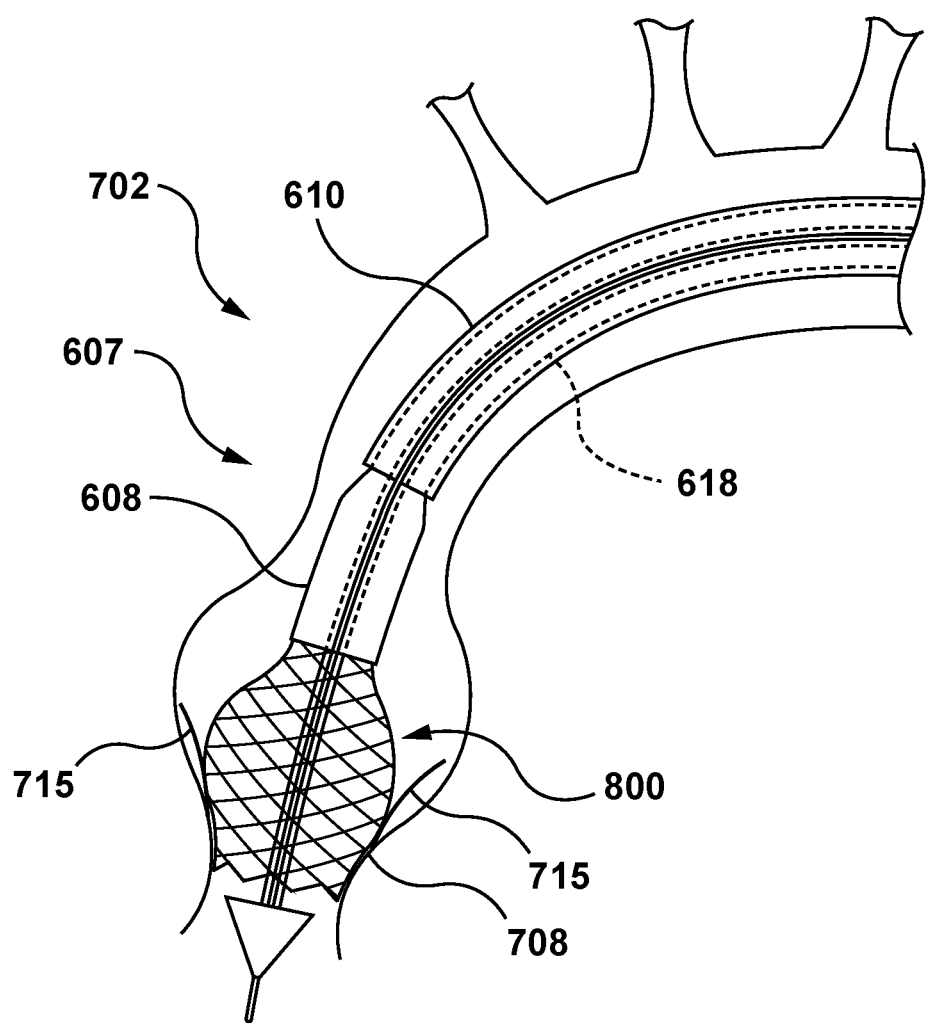
FIG. 14D is a simplified illustration of the delivery device of FIG. 2A and an expanding stented prosthetic heart valve.

With capsule 608 in the desired delivery location and centered on valve annulus 708, as shown in FIG. 14C, stented prosthetic heart valve 800 is now deployed. Actuator mechanism 644 of handle 640 (not shown in FIGS. 14A-14E) is operated proximally to retract capsule assembly 607. In particular, proximal shaft 618 and capsule 608 are moved proximally to withdraw capsule 608 from its position surrounding stented prosthetic heart valve 800, and retract capsule 608 into lumen 628 (not shown on FIGS. 14A-14E) of outer stability shaft 610, as shown in FIG. 14D. As capsule 608 is retracted proximally, capsule 608 transitions from the expanded configuration with outer diameter $OD_e$ to the collapsed configuration with outer diameter $OD_c$. As described previously, outer diameter $OD_c$ of capsule 608 is smaller than outer diameter $OD_e$ of capsule 608 and is also smaller than inner diameter $ID_a$ of outer stability shaft 610. As stented prosthetic heart valve 800 expands, it traps native leaflets 715 against the wall of valve annulus 708.

Figure 14E:
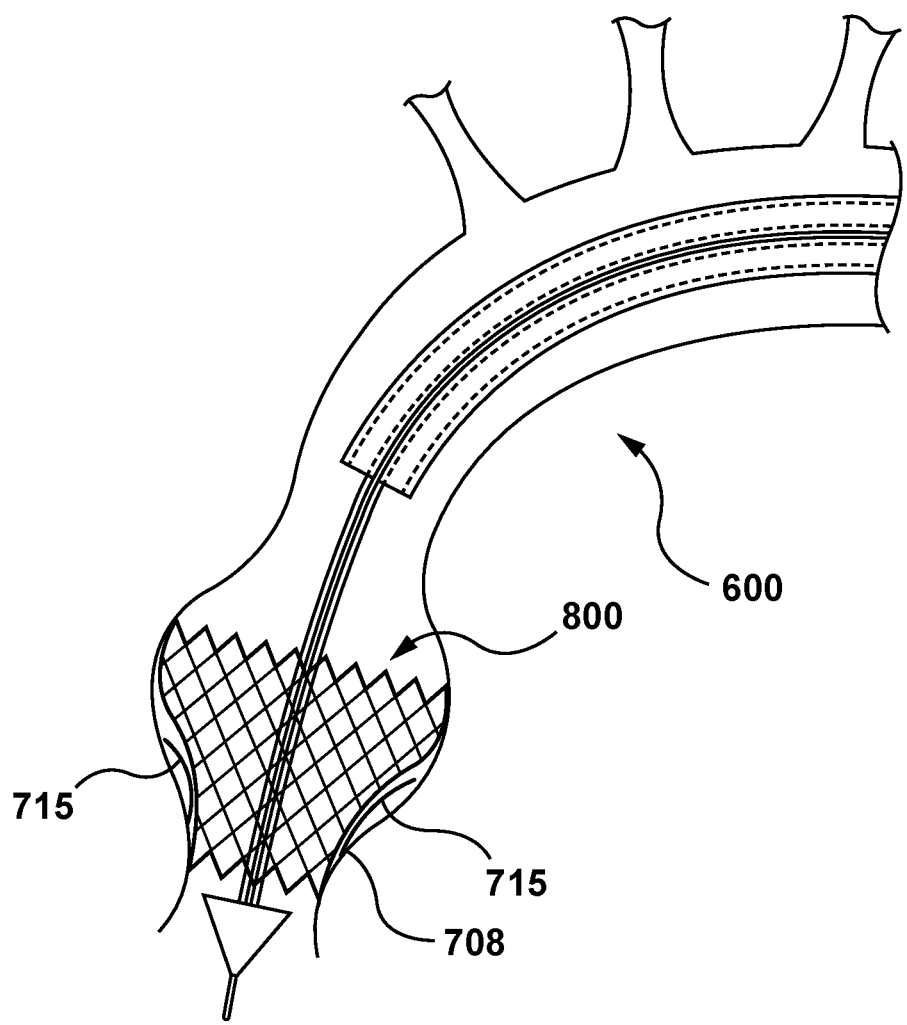
FIG. 14E is a simplified illustration of the delivery device of FIG. 2A and the stented prosthetic heart valve in a radially expanded deployed configuration.

Once stented prosthetic heart valve 800 is fully deployed and in the radially expanded deployed configuration, (with native valve leaflets 715 disposed between the wall of valve annulus 708 and an outer surface of stented prosthetic heart valve 800), as shown in FIG. 14E, delivery device 600 may be retracted and removed from the patient's vasculature using established procedures.

Figure 15:
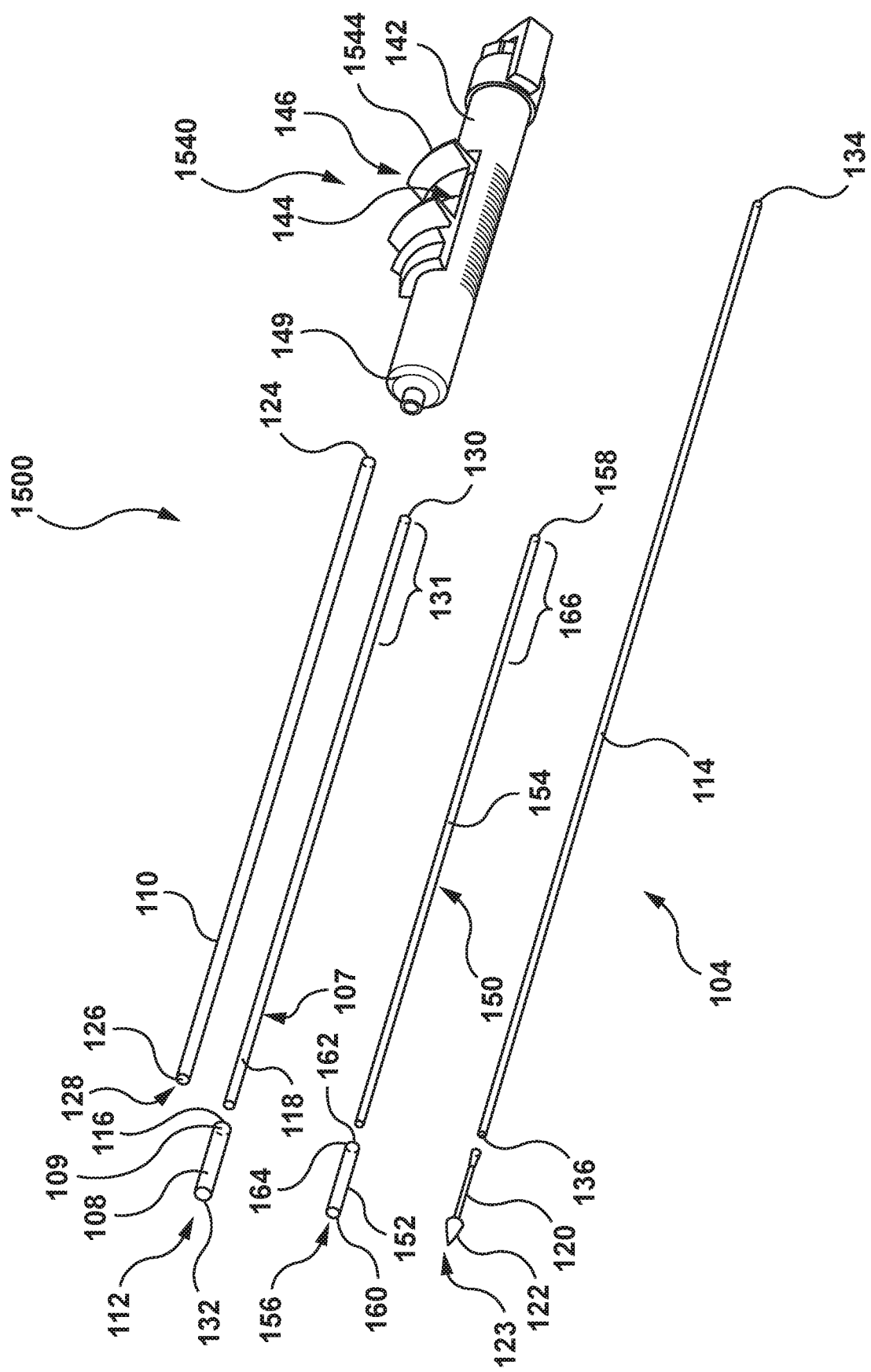
FIG. 15 is an exploded perspective illustration of a delivery device according to another embodiment hereof, wherein the delivery device includes the capsule of FIG. 2A as well as a second or delivery capsule.
Figure 16:
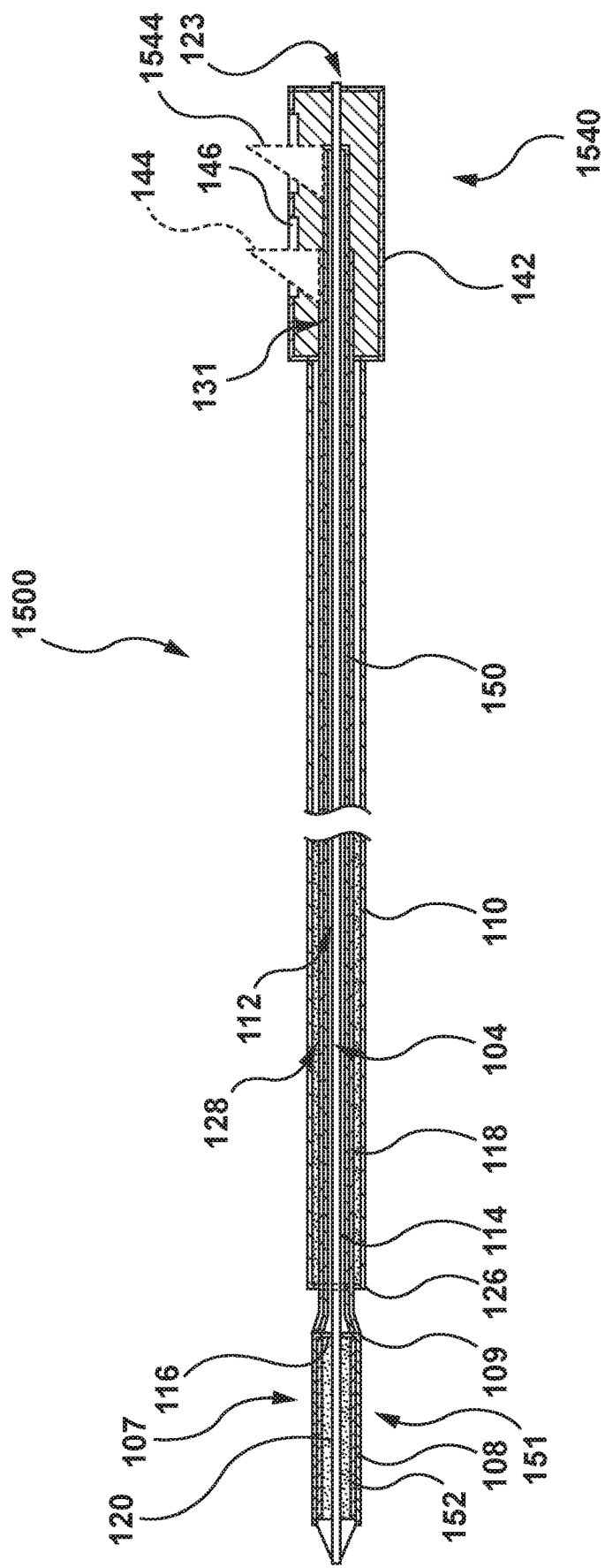
FIG. 16 is a cutaway illustration of the delivery device of FIG. 15, wherein both the capsule of FIG. 2A and the second or delivery capsule are in expanded configurations and disposed distal to the distal end of the outer stability shaft of the delivery device.

FIGS. 15-16 show a delivery device 1500 according to another embodiment hereof. Similar to delivery device 100, delivery device 1500 includes outer stability shaft 110, capsule assembly 107, and inner shaft assembly 104. Outer stability shaft 110, capsule assembly 107, and inner shaft assembly 104 of delivery device 1500 are described above with respect to delivery device 100, and therefore construction and description of these components will not be repeated in detail. However, unlike delivery device 100, delivery device 1500 further includes a delivery capsule assembly 150.

Delivery capsule assembly 150 is coaxially and slidably disposed between inner shaft assembly 104 and capsule assembly 107. Stated another way, delivery capsule assembly 150 may be longitudinally moved relative to inner shaft assembly 104, capsule assembly 107, and outer stability shaft 110. With reference to FIGS. 15-16, delivery capsule assembly 150 includes a delivery capsule 152 and a delivery shaft 154, and defines a lumen 156 extending from a proximal end 158 of delivery shaft 154 to a distal end 160 of delivery capsule 152. Although delivery capsule assembly 150 is described herein as including delivery capsule 152 and delivery shaft 154, delivery capsule 152 may simply be an extension of delivery shaft 154. The length and thickness of delivery capsule 152 are determined by the requirements of the specific application. Delivery shaft 154 is configured for fixed connection to delivery capsule 152 at a connection point 162 at a proximal end 164 of delivery capsule 152 for example, and not by way of limitation, by fusing, welding, adhesive, sutures, or other means suitable for the purposes described herein, and extends proximally from delivery capsule 152, with delivery shaft 154 configured for fixed connection to a handle 1540. Handle 1540 is similar to handle 140 described previously, except that handle 1540 includes a second actuator mechanism 1544 for actuating delivery capsule assembly 150. In an embodiment, second actuator mechanism 1544 extends through longitudinal slot 146 for interfacing by a user. Second actuator mechanism 1544 is generally constructed to provide selective retraction/advancement of delivery capsule assembly 150 and can have a variety of constructions and/or devices capable of providing the desired user interface. Second actuator mechanism 1544 is further described in U.S. Pat. No. 8,579,963 to Tabor, previously incorporated by reference.

More particularly, delivery shaft 154 of delivery capsule assembly 150 extends proximally into housing 142 of handle 1540 and a proximal portion 166 of delivery shaft 154 is rigidly connected to delivery actuator mechanism 1544 of handle 1540. Proximal portion 166 is coupled to delivery actuator mechanism 1544 such that movement of delivery actuator mechanism 1544 causes delivery capsule assembly 150 to move relative to outer stability shaft 110 capsule assembly 107, and inner shaft assembly 104. Delivery shaft 154 may be coupled to delivery actuator mechanism 1544, for example, and not by way of limitation by adhesives, welding, clamping, and other coupling devices as appropriate. Delivery capsule assembly 150 is thus movable relative to handle 1540, outer stability shaft 110, capsule assembly 107, and inner shaft assembly 104 by delivery actuator mechanism 1544. However, if delivery actuator mechanism 1544 is not moved and handle 1540 is moved, delivery capsule assembly 150 moves with handle 1540, not relative to handle 1540.

According to embodiments hereof, delivery capsule 152 is configured to be collapsible upon retraction thereof into capsule assembly 107. Delivery capsule 152 is a thin-walled capsule designed to minimize crossing profile of the stented prosthetic heart valve loaded therein for introduction into a body. Delivery capsule 152 may be formed of materials such as, but no limited to materials similar to those used in the construction of angioplasty balloons, such as polyethylene terephthalate (PET), nylon, or other materials suitable for the purposes described herein. FIG. 16 shows delivery device 1500 with delivery capsule 152 in the expanded configuration, in which a stented prosthetic heart valve (not shown) is held in a radially compressed delivery configuration therein. Stated another way, delivery capsule 152 in the expanded configuration functions to retain or hold the stented prosthetic heart valve in the radially compressed configuration for delivery thereof. When retracted, delivery capsule 152 collapses into capsule assembly 107 due to the thin-walled material of delivery capsule 152. Thus, delivery capsule 152 transitions from the expanded configuration to the collapsed configuration when retracted into capsule assembly 107. Delivery capsule 152 retracts into lumen 112 of capsule assembly 107 such that delivery capsule 152 does not surround the stented prosthetic heart valve, and the stented prosthetic heart valve radially expands to its radially expanded deployed configuration.

Capsule assembly 107 is coaxially and slidably disposed between delivery capsule assembly 150 and outer stability shaft 110. In an embodiment, capsule assembly 107 and more specifically capsule 108 may be utilized to provide additional support to delivery capsule 152 during tracking through a vasculature to a treatment site. For example, delivery capsule 152 having a minimized crossing profile may be disposed over a stented prosthetic heart valve during introduction into the body and capsule 108 may be in its collapsed configuration within outer stability shaft 110 during introduction into the body. After introduction into the body, capsule 108 may be advanced from the collapsed configuration within outer stability shaft 110 until capsule 108 is in its expanded configuration and disposed over delivery capsule 152 to provide additional support during advancement to the treatment site. FIG. 16 shows delivery device 1500 with delivery capsule 152 in the expanded configuration, in which a stented prosthetic heart valve (not shown) is held in a radially compressed delivery configuration therein, and capsule 108 is also in the expanded configuration and disposed over delivery capsule 152.

In another embodiment, capsule assembly 107 and more specifically capsule 108 is configured for recapture of a partially deployed stented prosthetic heart valve. More particularly, in situations where the stented prosthetic heart valve is partially released from delivery capsule 152 and recapture by the weaker (relative to capsule 108) delivery capsule 152 is not possible at body temperature, the stronger (relative to delivery capsule 152) capsule 108 may be advanced to recapture the partially deployed stented prosthetic heart valve. Thus, delivery capsule 152 having a minimized crossing profile is utilized for radially collapsing a stented prosthetic heart valve and tracking it through a vasculature, while capsule 108 is utilized on an as-needed basis for recapture and repositioning of a partially deployed stented prosthetic heart valve.

In embodiments described above, capsule 108 in the expanded configuration functions to retain or hold the stented prosthetic heart valve in a radially compressed configuration for delivery thereof. However, in other embodiments, capsule 108 may utilized solely in a protective manner for the stented prosthetic heart valve and other means may be utilized for expanding the stented prosthetic heart valve. For example, in another embodiment hereof, capsule 108 is configured to protect a balloon expandable stented prosthetic heart valve and the surrounding native anatomy as capsule 108 with the stented prosthetic heart valve disposed therein is advanced to a treatment site. Thus, capsule 108 is for protection only, as the stented prosthetic heart valve is not self-expanding and therefore does not require the capsule 108 to radially collapse and restrain the stented prosthetic heart valve when disposed therein. Once the stented prosthetic heart valve is at the treatment site, the capsule assembly 107 is retracted to expose the stented prosthetic heart valve. The stented prosthetic heart valve may then be steered to the desired treatment position and expanded by balloon inflation, as will be understood by one skilled in the art. In yet another embodiment, the stented prosthetic heart valve is self-expanding and restrained by a cinch mechanism or sutures for delivery to a desired treatment site. Examples of suitable cinch mechanisms for retaining self-expanding valve prostheses are described in U.S. Patent Publication No. 2014/0330368 to Gloss, which is incorporated herein by reference in its entirety. In such an embodiment, capsule 108 is configured only for protection of the stented prosthetic heart valve and the native anatomy during introduction and advancement of the stented prosthetic heart valve to the treatment site. Once the stented prosthetic heart valve is at the treatment site, capsule assembly 107 is retracted and collapsed in outer stability shaft 110 to expose the stented prosthetic heart valve. The stented prosthetic heart valve is then deployed at the treatment site by releasing the sutures such that the stented prosthetic heart valve radially expands at the treatment site.

While only some embodiments have been described herein, it should be understood that it has been presented by way of illustration and example only, and not limitation. Various changes in form and detail can be made therein without departing from the spirit and scope of the invention, and each feature of the embodiment discussed herein, and of each reference cited herein, can be used in combination with the features of any other embodiment. All patents and publications discussed herein are incorporated by reference herein in their entirety.

What is claimed is:

1. A delivery device for percutaneously delivering a stented prosthetic heart valve, the stented prosthetic heart valve being radially expandable from a radially compressed delivery configuration to a radially expanded deployed configuration, the delivery device comprising:
   a capsule assembly, wherein the capsule assembly includes a capsule and a proximal shaft coupled to a proximal end of the capsule, the capsule including an expanded configuration wherein the capsule has a first outer diameter and a collapsed configuration wherein the capsule has a second outer diameter smaller than the first outer diameter;
   a handle including a housing and an actuator mechanism, wherein the actuator mechanism is coupled to a proximal portion of the proximal shaft and is configured to selectively move the proximal shaft and the capsule relative to the housing to release the stented prosthetic heart valve; and
   an outer stability shaft defining a lumen, the outer stability shaft coupled to the handle and configured to receive the proximal shaft within the lumen of the outer stability shaft, the outer stability shaft having an inner diameter, wherein the first outer diameter of the capsule is greater than the inner diameter of the outer stability shaft and the second outer diameter of the capsule is smaller than the inner diameter of the outer stability shaft, and wherein the capsule in the expanded configuration has an inner diameter along an entire length of the capsule that is not greater than an outer diameter of the outer stability shaft.

2. The delivery device of claim 1, wherein the proximal end of the capsule is disposed distal to the outer stability shaft when the capsule is in the expanded configuration with the first outer diameter and the capsule is retracted within the lumen of the outer stability shaft when the capsule is in the collapsed configuration with the second outer diameter.

3. The delivery device of claim 2, wherein the capsule is formed from a shape memory material including a pre-set shape.

4. The delivery device of claim 3, wherein the pre-set shape includes the capsule in the collapsed configuration with the second outer diameter and the capsule is configured to be expanded to the first outer diameter.

5. The delivery device of claim 3, wherein the pre-set shape includes the capsule in the expanded configuration with the first outer diameter and the capsule is configured to be compressed to the second outer diameter as the capsule is retracted into the lumen of the outer stability shaft.

6. The delivery device of claim 3, wherein the capsule comprises a circumferentially continuous layer, an elastic frame, and a non-circumferentially continuous layer connected to the elastic frame and to the circumferentially continuous layer, the non-circumferentially continuous layer having a longitudinal gap when at the first outer diameter.

7. The delivery device of claim 2, wherein the capsule comprises a polymeric material and a plurality of longitudinal reinforcing members coupled to the polymeric material.

8. The delivery device of claim 7, wherein when the capsule is in the collapsed configuration with the second outer diameter the polymeric material folds between the longitudinal reinforcing members, and when the capsule is in the expanded configuration with the first outer diameter the polymeric material forms a cylinder.

9. The delivery device of claim 1, further comprising a steering mechanism coupled to the outer stability shaft such that the outer stability shaft is steerable.

10. The delivery device of claim 1, wherein the proximal end of the capsule is disposed directly adjacent to a distal end of the stability shaft when the capsule is in the expanded configuration.

11. A delivery device for percutaneously delivering a stented prosthetic heart valve, the stented prosthetic heart valve being radially expandable from a radially compressed delivery configuration to a radially expanded deployed configuration, the delivery device comprising:
a capsule assembly, wherein the capsule assembly includes a capsule and a proximal shaft coupled to a proximal end of the capsule, the capsule including an expanded configuration wherein the capsule is configured to compressively constrain the stented prosthetic heart valve in the radially compressed delivery configuration during delivery thereof through a vasculature, and a collapsed configuration wherein the capsule is configured to not surround the stented prosthetic heart valve;
a handle including a housing and an actuator mechanism, wherein the actuator mechanism is coupled to a proximal portion of the proximal shaft and is configured to selectively move the proximal shaft and the capsule relative to the housing to release the stented prosthetic heart valve; and
an outer stability shaft defining a lumen, the outer stability shaft coupled to the handle and configured to receive the proximal shaft within the lumen of the outer stability shaft, wherein the proximal end of the capsule is disposed distal to a distal end of the outer stability shaft when the capsule is in the expanded configuration and the capsule is disposed within the lumen of the outer stability shaft when the capsule is in the collapsed configuration;
wherein the capsule includes a first outer diameter when in the expanded configuration and a second outer diameter when in the collapsed configuration, wherein the second outer diameter is smaller than the first outer diameter and the second outer diameter is smaller than an inner diameter of the outer stability shaft;
wherein the capsule is formed from a shape memory material including a pre-set shape;
wherein the pre-set shape includes the capsule in the collapsed configuration and the capsule is configured to be expanded to the expanded configuration to receive the stented prosthetic heart valve.

12. The delivery device of claim 11, wherein the capsule comprises a circumferentially continuous layer, an elastic frame, and a non-circumferentially continuous layer connected to the elastic frame and to the circumferentially continuous layer, the non-circumferentially continuous layer having a longitudinal gap in the expanded configuration.

13. The delivery device of claim 11, wherein the capsule comprises a thin walled polymeric material and a plurality of longitudinal reinforcing members coupled to the thin walled polymeric material.

14. The delivery device of claim 13, wherein when the capsule is in the collapsed configuration, the polymeric material folds between the longitudinal reinforcing members and when the capsule is in the expanded configuration, the polymeric material forms a cylinder.

15. The delivery device of claim 11, further comprising a steering mechanism coupled to the outer stability shaft such that the outer stability shaft is steerable.

16. The delivery device of claim 11, wherein the proximal end of the capsule is disposed directly adjacent to the distal end of the stability shaft when the capsule is in the expanded configuration.

* * * * *